(12) United States Patent
Brugger et al.

(10) Patent No.: US 7,780,619 B2
(45) Date of Patent: Aug. 24, 2010

(54) BLOOD TREATMENT APPARATUS

(75) Inventors: James M. Brugger, Newburyport, MA (US); Jeffrey H. Burbank, Boxford, MA (US); Dennis M Treu, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 12/021,872

(22) Filed: Jan. 29, 2008

(65) Prior Publication Data

US 2008/0149551 A1 Jun. 26, 2008

Related U.S. Application Data

(60) Continuation of application No. 11/163,773, filed on Oct. 31, 2005, now abandoned, and a division of application No. 10/041,949, filed on Jan. 7, 2002, now Pat. No. 6,979,309, and a continuation-in-part of application No. 10/913,815, filed on Aug. 6, 2004, now Pat. No. 7,347,849, and a division of application No. 09/865,905, filed on May 24, 2001, now Pat. No. 6,852,090, and a continuation of application No. 09/513,773, filed on Feb. 25, 2000, now Pat. No. 6,579,253, and a division of application No. 09/451,238, filed on Nov. 29, 1999, now abandoned.

(51) Int. Cl.
*A61M 37/00* (2006.01)
*B01D 29/00* (2006.01)

(52) U.S. Cl. ............... 604/4.01; 604/5.01; 210/252

(58) Field of Classification Search ....... 604/4.01–6.16, 604/408, 29; 422/44–48; 210/650–652, 210/645, 646

See application file for complete search history.

(56) References Cited

U.S. PATENT DOCUMENTS 3,709,222 A 1/1973 DeVries (Continued)

FOREIGN PATENT DOCUMENTS

CA 1158988 12/1983

(Continued)

OTHER PUBLICATIONS

Baldamus et al., "Outcome of Long Term Hemofiltration," International Society of Nephrology, Dec. 28, 1994, pp. S-41-s46.

(Continued)

*Primary Examiner*—Leslie R Deak
*Assistant Examiner*—Philip R Wiest
(74) *Attorney, Agent, or Firm*—Miles & Stockbridge P.C.; Mark A. Catan, Esq.; Michael A. Minter, Esq.

(57) ABSTRACT

A blood processing machine has a compact configuration in which the first and second parts of the machine separate to open a gap between them. The actuators and sensors face into the gap such that when a cartridge with a fluid circuit is placed in the gap and the two parts are brought together closing the gap, the actuators and sensor engage the fluid circuit. One of the parts has an operator interface with a display that is preferably aligned with the gap in such a way that the frontal area of the machine is minimized.

21 Claims, 14 Drawing Sheets

U.S. PATENT DOCUMENTS

| | | |
|---|---|---|
| 3,774,762 A | 11/1973 | Lichtenstein |
| 3,902,030 A | 8/1975 | Popa |
| 3,912,455 A | 10/1975 | Lichtenstein |
| 4,069,968 A | 1/1978 | Herman |
| 4,127,481 A | 11/1978 | Malchesky et al. |
| 4,181,132 A | 1/1980 | Parks |
| 4,275,726 A | 6/1981 | Schael |
| 4,370,983 A | 2/1983 | Lichtenstein |
| 4,379,452 A | 4/1983 | DeVries |
| 4,396,383 A | 8/1983 | Hart |
| 4,464,172 A | 8/1984 | Lichtenstein |
| 4,468,329 A | 8/1984 | Shaldon et al. |
| 4,469,593 A | 9/1984 | Ishihara et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,507,114 A | 3/1985 | Bohman et al. |
| 4,514,295 A | 4/1985 | Mathieu et al. |
| 4,526,515 A | 7/1985 | DeVries |
| 4,537,561 A | 8/1985 | Xanthopoulos |
| 4,576,603 A | 3/1986 | Moss |
| 4,610,781 A | 9/1986 | Bilstad et al. |
| 4,614,590 A | 9/1986 | Rath et al. |
| 4,617,115 A | 10/1986 | Vantard |
| 4,629,448 A | 12/1986 | Carlsson et al. |
| 4,666,598 A | 5/1987 | Heath et al. |
| 4,670,007 A | 6/1987 | Wheeldon et al. |
| 4,683,053 A | 7/1987 | Polaschegg |
| 4,692,138 A | 9/1987 | Troutner et al. |
| 4,702,829 A | 10/1987 | Polaschegg et al. |
| 4,711,715 A | 12/1987 | Polaschegg |
| 4,713,171 A | 12/1987 | Polaschegg |
| 4,737,140 A | 4/1988 | Lee et al. |
| 4,756,705 A | 7/1988 | Beijbom et al. |
| 4,765,888 A | 8/1988 | Barthe et al. |
| 4,770,787 A | 9/1988 | Heath et al. |
| 4,776,964 A | 10/1988 | Schoendorfer et al. |
| 4,808,167 A | 2/1989 | Mann et al. |
| 4,824,339 A | 4/1989 | Bainbridge et al. |
| 4,851,126 A | 7/1989 | Schoendorfer |
| 4,857,199 A | 8/1989 | Cortial |
| 4,885,001 A | 12/1989 | Leppert |
| 4,886,431 A | 12/1989 | Soderquist et al. |
| 4,892,518 A | 1/1990 | Cupp et al. |
| 4,894,150 A | 1/1990 | Schurek et al. |
| 4,894,164 A | 1/1990 | Polaschegg |
| 4,899,057 A | 2/1990 | Koji |
| 4,909,931 A | 3/1990 | Bibi |
| 4,923,598 A | 5/1990 | Schal |
| 4,950,395 A | 8/1990 | Richalley |
| 4,966,579 A | 10/1990 | Polaschegg |
| 4,997,570 A | 3/1991 | Polaschegg |
| 5,006,110 A | 4/1991 | Garrison et al. |
| 5,041,098 A | 8/1991 | Loiterman et al. |
| 5,047,147 A | 9/1991 | Chevallet et al. |
| 5,056,059 A | 10/1991 | Tivig et al. |
| 5,062,774 A | 11/1991 | Kramer et al. |
| 5,108,063 A | 4/1992 | Koerber, Sr. et al. |
| 5,114,580 A | 5/1992 | Ahmad et al. |
| 5,125,891 A | 6/1992 | Hossain et al. |
| 5,151,082 A | 9/1992 | Gorsuch et al. |
| 5,187,641 A | 2/1993 | Muskatello et al. |
| 5,204,681 A | 4/1993 | Greene |
| 5,211,849 A | 5/1993 | Kitaevich et al. |
| 5,230,702 A | 7/1993 | Lindsay et al. |
| 5,247,434 A | 9/1993 | Peterson et al. |
| 5,277,820 A | 1/1994 | Ash |
| 5,291,205 A | 3/1994 | Greene |
| 5,330,415 A | 7/1994 | Storti et al. |
| 5,330,448 A | 7/1994 | Chu |
| 5,344,568 A | 9/1994 | Kitaevich et al. |
| 5,350,357 A * | 9/1994 | Kamen et al. .................. 604/29 |
| 5,360,395 A | 11/1994 | Utterberg |
| 5,417,222 A | 5/1995 | Dempsey et al. |
| 5,423,769 A | 6/1995 | Jonkman et al. |
| 5,441,636 A | 8/1995 | Chevallet et al. |
| 5,445,506 A | 8/1995 | Afflerbaugh et al. |
| 5,462,416 A | 10/1995 | Dennehey et al. |
| 5,472,614 A | 12/1995 | Rossi |
| 5,476,592 A | 12/1995 | Simard |
| 5,484,397 A | 1/1996 | Twardowski |
| 5,486,286 A | 1/1996 | Peterson et al. |
| 5,487,827 A | 1/1996 | Peterson et al. |
| 5,522,998 A | 6/1996 | Polaschegg |
| 5,536,412 A | 7/1996 | Ash |
| 5,562,617 A | 10/1996 | Finch, Jr. et al. |
| 5,569,463 A | 10/1996 | Helmus et al. |
| 5,578,223 A | 11/1996 | Bene et al. |
| 5,581,257 A | 12/1996 | Greene et al. |
| 5,614,677 A | 3/1997 | Wamsiedler et al. |
| 5,616,305 A | 4/1997 | Mathieu |
| 5,679,245 A | 10/1997 | Manica |
| 5,690,831 A | 11/1997 | Kenley et al. |
| 5,693,008 A | 12/1997 | Brugger et al. |
| 5,698,090 A | 12/1997 | Bene et al. |
| 5,702,597 A | 12/1997 | Chevallet et al. |
| 5,725,776 A | 3/1998 | Kenley et al. |
| 5,730,713 A | 3/1998 | Okarma et al. |
| 5,744,027 A | 4/1998 | Connell et al. |
| 5,762,805 A | 6/1998 | Truitt et al. |
| 5,776,345 A | 7/1998 | Truitt et al. |
| 5,799,690 A | 9/1998 | Jacobsen et al. |
| 5,808,181 A | 9/1998 | Wamsiedler et al. |
| 5,836,908 A | 11/1998 | Beden et al. |
| 5,838,908 A | 11/1998 | Matzke et al. |
| 5,846,419 A | 12/1998 | Nederlof |
| 5,858,238 A | 1/1999 | McRea et al. |
| 5,863,421 A | 1/1999 | Peter et al. |
| 5,865,749 A | 2/1999 | Doten et al. |
| 5,870,805 A | 2/1999 | Kandler et al. |
| 5,871,694 A | 2/1999 | Beden et al. |
| 5,902,336 A | 5/1999 | Mishkin |
| 5,910,252 A | 6/1999 | Truitt et al. |
| 5,919,154 A | 7/1999 | Toavs et al. |
| 5,919,369 A | 7/1999 | Ash |
| 5,923,001 A | 7/1999 | Morris et al. |
| 5,944,709 A | 8/1999 | Barney et al. |
| 5,951,870 A | 9/1999 | Utterberg |
| 6,022,335 A | 2/2000 | Ramadan |
| 6,039,877 A | 3/2000 | Chevallet et al. |
| 6,042,784 A | 3/2000 | Wamsiedler et al. |
| 6,113,554 A | 9/2000 | Gilcher et al. |
| 6,135,949 A | 10/2000 | Russo et al. |
| 6,149,294 A | 11/2000 | Jonsson et al. |
| 6,171,237 B1 | 1/2001 | Avitall et al. |
| 6,186,752 B1 * | 2/2001 | Deniega et al. .............. 417/475 |
| 6,188,988 B1 | 2/2001 | Barry et al. |
| 6,264,830 B1 | 7/2001 | Plester et al. |
| 6,302,844 B1 | 10/2001 | Walker et al. |
| 6,406,631 B1 | 6/2002 | Collins et al. |
| 6,554,789 B1 | 4/2003 | Brugger et al. |
| 6,579,253 B1 | 6/2003 | Burbank et al. |
| 6,582,387 B2 | 6/2003 | Derek et al. |
| 6,589,482 B1 | 7/2003 | Burbank et al. |
| 6,595,943 B1 | 7/2003 | Burbank |
| 6,622,542 B2 | 9/2003 | Derek et al. |
| 6,638,477 B1 | 10/2003 | Treu et al. |
| 6,638,478 B1 | 10/2003 | Treu et al. |
| 6,641,533 B2 | 11/2003 | Causey, III et al. |
| 6,673,314 B1 | 1/2004 | Burbank et al. |
| 6,695,803 B1 * | 2/2004 | Robinson et al. .......... 604/4.01 |
| 6,716,356 B2 | 4/2004 | Collins et al. |
| 6,743,201 B1 | 6/2004 | Donig et al. |
| 6,764,761 B2 | 7/2004 | Eu et al. |

| | | |
|---|---|---|
| 6,814,547 B2 | 11/2004 | Childers et al. |
| 6,817,984 B2 | 11/2004 | Robinson et al. |
| 6,830,553 B1 | 12/2004 | Burbank et al. |
| 6,852,090 B2 | 2/2005 | Burbank et al. |
| 6,905,314 B2 | 6/2005 | Danby |
| 6,955,655 B2 | 10/2005 | Burbank et al. |
| 6,979,309 B2 | 12/2005 | Burbank et al. |
| 7,147,613 B2 | 12/2006 | Burbank et al. |
| 7,175,606 B2 | 2/2007 | Bowman, Jr. et al. |
| 7,267,658 B2 | 9/2007 | Treu et al. |
| 7,300,413 B2 | 11/2007 | Burbank et al. |
| 7,338,460 B2 | 3/2008 | Burbank et al. |
| 7,347,849 B2 | 3/2008 | Brugger et al. |
| 2001/0016699 A1 | 8/2001 | Burbank et al. |
| 2002/0147423 A1 | 10/2002 | Burbank et al. |
| 2003/0217957 A1 | 11/2003 | Bowman et al. |
| 2003/0220605 A1 | 11/2003 | Bowman et al. |
| 2003/0220606 A1 | 11/2003 | Busby et al. |
| 2003/0220607 A1 | 11/2003 | Busby et al. |
| 2003/0220608 A1 | 11/2003 | Huitt et al. |
| 2004/0015819 A1 | 1/2004 | Romano-Critchley et al. |
| 2004/0019313 A1 | 1/2004 | Childers et al. |
| 2004/0127840 A1 | 7/2004 | Gara et al. |
| 2004/0138607 A1 | 7/2004 | Burbank et al. |
| 2004/0158190 A1 | 8/2004 | Duchamp et al. |
| 2004/0162513 A1 | 8/2004 | Neri et al. |
| 2004/0167457 A1 | 8/2004 | Tonelli et al. |
| 2004/0186416 A1 | 9/2004 | Caleffi |
| 2004/0243047 A1 | 12/2004 | Brugger et al. |
| 2004/0243048 A1 | 12/2004 | Brugger et al. |
| 2004/0243049 A1 | 12/2004 | Brugger et al. |
| 2004/0249330 A1 | 12/2004 | Treu |
| 2005/0015070 A1 | 1/2005 | Delnevo et al. |
| 2005/0020958 A1 | 1/2005 | Paolini et al. |
| 2005/0045540 A1 | 3/2005 | Connell et al. |
| 2005/0045548 A1 | 3/2005 | Brugger et al. |
| 2005/0061740 A1 | 3/2005 | Felding et al. |
| 2005/0065459 A1 | 3/2005 | Zhang et al. |
| 2005/0070837 A1 | 3/2005 | Ferrarini et al. |
| 2005/0082210 A1 | 4/2005 | Favre |
| 2005/0090774 A1 | 4/2005 | Tonelli et al. |
| 2005/0113734 A1 | 5/2005 | Brugger et al. |
| 2005/0113735 A1 | 5/2005 | Brugger et al. |
| 2005/0126998 A1 | 6/2005 | Childers |
| 2005/0171501 A1 | 8/2005 | Kelly |
| 2005/0197612 A1 | 9/2005 | Levin et al. |
| 2005/0209563 A1 | 9/2005 | Hopping et al. |
| 2005/0230292 A1 | 10/2005 | Beden et al. |
| 2005/0251086 A1 | 11/2005 | Sternby |
| 2006/0084906 A1 | 4/2006 | Burbank et al. |

FOREIGN PATENT DOCUMENTS

| | | |
|---|---|---|
| FR | 2684879 | 6/1993 |
| GB | 2246718 | 2/1992 |
| WO | WO 98/30258 | 7/1998 |
| WO | WO 98/35710 | 8/1998 |
| WO | WO 98/52628 | 11/1998 |
| WO | WO 99/42150 | 8/1999 |
| WO | WO 00/02603 | 1/2000 |
| WO | WO 01/37786 | 5/2001 |

OTHER PUBLICATIONS

Canaud et al., "Failure of a daily haemofiltration programme using a highly permeable membrane to return $\beta_2$-microglobulin concentrations to normal in haemodialysis patients," Nephrol Dialysis Transplantation 7:924-930.

Summary of Collins et al., "Clinical Comparison of Hemodialysis and Hemofiltration," Kidney Int Suppl Dec. 1985; 17: S18-22.

Diapact CRRT Operating Manual Version 2.2—Mar. 1998, M. Braun Melsungen AG.

Manns et al., "The acu-men: A new device for continuous renal replacement therapy in acute renal failure," Kidney International, vol. 54, 1998, pp. 268-274.

Prisma System Operator's Manual Feb. 1997, Gambro Healthcare.

Quellhorst et al., "Long-Term Morbidity: Hemofiltration vs. Hemodialysis," Dialysis Membranes: Structure and Predictions Contrib Nephrol. Base, Karger, 1995, vol. 13, pp. 110-119.

Quellhorst et al., "Postdilution Hemofiltration is Rational and Preferable," Proc. Dialysis Transplant Forum, 1979 pp. 54-58.

Schaefer et al., "Chronic Hemofiltration a Critical Evaluation of a New Method for the Treatment of Blood," Artificial Organs, vol. 2 No. 4, pp. 386-394.

Abstract for Weiss et al., "Four years' experience of long-term hemofiltration in a Swedish Center," Scand J Urol Nephrol 1989; 23(3):223-9.

* cited by examiner

BLOOD TREATMENT APPARATUS

RELATED APPLICATIONS

This application is a continuation of co-pending U.S. patent application Ser. No. 11/163,773, filed Oct. 31, 2005, which is a divisional of U.S. patent application Ser. No. 10/041,949, filed Jan. 7, 2002, now U.S. Pat. No. 6,979,309; and a continuation-in-part of co-pending U.S. patent application Ser. No. 10/913,815, filed Aug. 6, 2004, which is a divisional U.S. patent application Ser. No. 09/865,905, filed May 24, 2001, now U.S. Pat. No. 6,852,090; which is a continuation of U.S. patent application Ser. No. 09/513,773, filed Feb. 25, 2000, now U.S. Pat. No. 6,579,253, which is a divisional of U.S. patent application Ser. No. 09/451,238, filed Nov. 29, 1999, now abandoned.

FIELD OF THE INVENTION

This invention relates to systems and methods for processing blood, e.g., for filtration, pheresis, or other diagnostic or therapeutic purposes.

BACKGROUND OF THE INVENTION

There are many types of blood processing and fluid exchange procedures, each providing different therapeutic effects and demanding different processing criteria. Typically, such procedures entail the removal of blood or another fluid from an individual and the return of blood or another fluid to the individual in a controlled fashion. Examples of such procedures include hemofiltration (HF), hemodialysis (HD), hemodialysis with hemofiltration (HDF), and peritoneal dialysis (PD).

In carrying out these procedures, specially designed fluid circuits, which can be complex and convoluted, are placed into a prescribed operative association with pumps, clamps, and sensors, which are typically mounted on a machine that is also specially designed to carry out the intended procedure. Numerous safety and control elements of the fluid circuit and the machine must be placed in operative association in order to carry out the procedure in the intended way. As a consequence, the process of loading a fluid circuit on the machine can be tedious and error-prone.

There is a need for simplicity and convenience when loading a fluid circuit in a prescribed way in association with safety and control elements on a blood and/or fluid processing machine.

Typically, when performing the blood processing and fluid exchange procedures of the type just described, a replacement or make-up fluid is returned back to the individual in some proportion to the amount of fluid that is removed from the individual. The type and make-up of fluids that these procedures handle vary according to the particular treatment modality being performed, e.g., among waste fluid and replacement fluid (in HF or HDF); or replacement fluid and dialysis solution (in HD or HDF); or fresh peritoneal dialysis solution and spent peritoneal dialysis solution (in PD. Controlled balancing of fluid amounts can be achieved by monitoring the weights of fluid removed and replacement or makeup fluid. However, weight sensing itself requires additional fluid circuit elements (e.g., weigh containers), additional hardware elements (e.g., weigh scales), as well as additional processing control and feedback features. These items add further complexity to the systems and their operation.

There is also a need for simplicity and convenience when undertaking a controlled balancing of fluids during a blood processing and/or fluid exchange procedure.

SUMMARY OF THE INVENTION

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

I. System Overview

Figure 1:
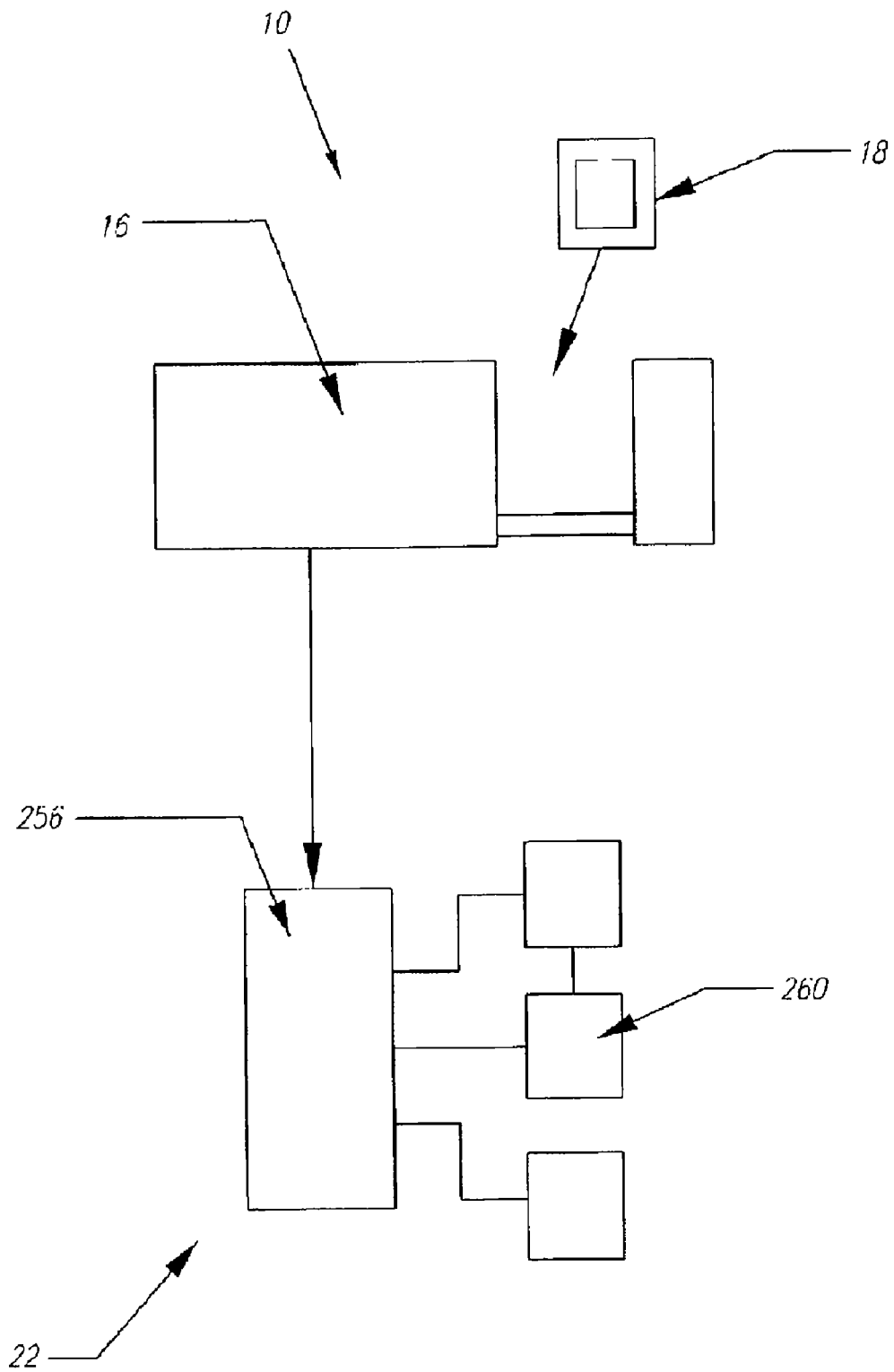
FIG. 1 is a diagrammatic view of a system that includes a machine and fluid processing cartridge that, in use, is mounted on the machine for conducting various types of blood processing and/or fluid exchange procedures.

FIG. 1 shows a system 10 that is well suited for handling fluids in support of various types of blood processing and/or fluid exchange procedures. The system 10 includes a durable hardware component or machine 16 (see FIG. 2) and a removable fluid processing cartridge 18 (see FIG. 3) that is intended to be installed in operative association with the machine 16 for use (see FIGS. 4 to 6).

The system 10 is suitable for use in many diverse treatment modalities during which blood and/or fluid are conveyed to and from an animal body. In particular, the system 10 is well suited for treatment modalities during which one fluid is removed from the body and replaced with another fluid in a controlled fashion. Such modalities include, e.g., hemofiltration (HF), hemodialysis (HD), hemodialysis with hemofiltration (HDF), and peritoneal dialysis (PD).

For example, the system 10 can perform hemofiltration, e.g., to treat an individual whose renal function is impaired or lacking, according to different selected protocols. The system 10 can be adapted to perform hemofiltration at relatively high blood flow rates to enable relatively short session time intervals, as well as at lower blood flow rates and over longer session time intervals. The former protocol can be adopted to achieve hemofiltration three or more times a week. The latter protocol can be adapted to achieve an overnight treatment regime, which can be called "nightly hemofiltration." Nightly hemofiltration can be conducted at intervals less or more frequent than three times a week. Alternatively, the system 10 can be adapted to perform hemofiltration on an acute basis, or on an intermittent chronic basis, at virtually any prescribed time interval and treatment pattern that achieves the maintenance of uremic toxin levels within a comfortable range. Thus, the system 10 can be adapted to perform multiple hemofiltration treatments per day at varying session times, morning, afternoon, or night, or a combination thereof.

The system 10 can also just as readily be adapted to perform hemodialysis (HD) or hemodialysis with hemofiltration (HDF). The fluid balancing functions that the system 10 can perform, as will be described in greater detail later, can also be readily adapted for use, either individually or in combination, in systems intended to perform prescribed peritoneal dialysis modalities.

The type and make-up of fluids that the system 10 can balance can and will vary according to the particular treatment modality being performed, e.g., among waste fluid and replacement fluid (in HF or HDF); or replacement fluid and dialysis solution (in HD or HDF); or fresh peritoneal dialysis solution and spent peritoneal dialysis solution (in PD). The terminology employed in this Specification in characterizing a particular type or make-up of fluid, or as ascribing a source, destination, or direction of fluid flow in the context of describing one treatment modality is not intended to be interpreted as being limited to that particular type or make up of fluid or that particular flow source, destination, or direction. Rather, a person of skill in the art will readily appreciate that the fluid type and make up and the flow particulars relating to volumetric fluid balancing can vary with different treatment modalities.

A. Fluid Processing Machine

The machine 16 (see FIG. 2) is preferably lightweight and portable, presenting a compact footprint, suited for operation on a table top or other relatively small surface normally found, e.g., in a hospital room or in a home. The compact size of the machine 16 also makes it well suited for shipment to a remote service depot for maintenance and repair.

Figure 2:
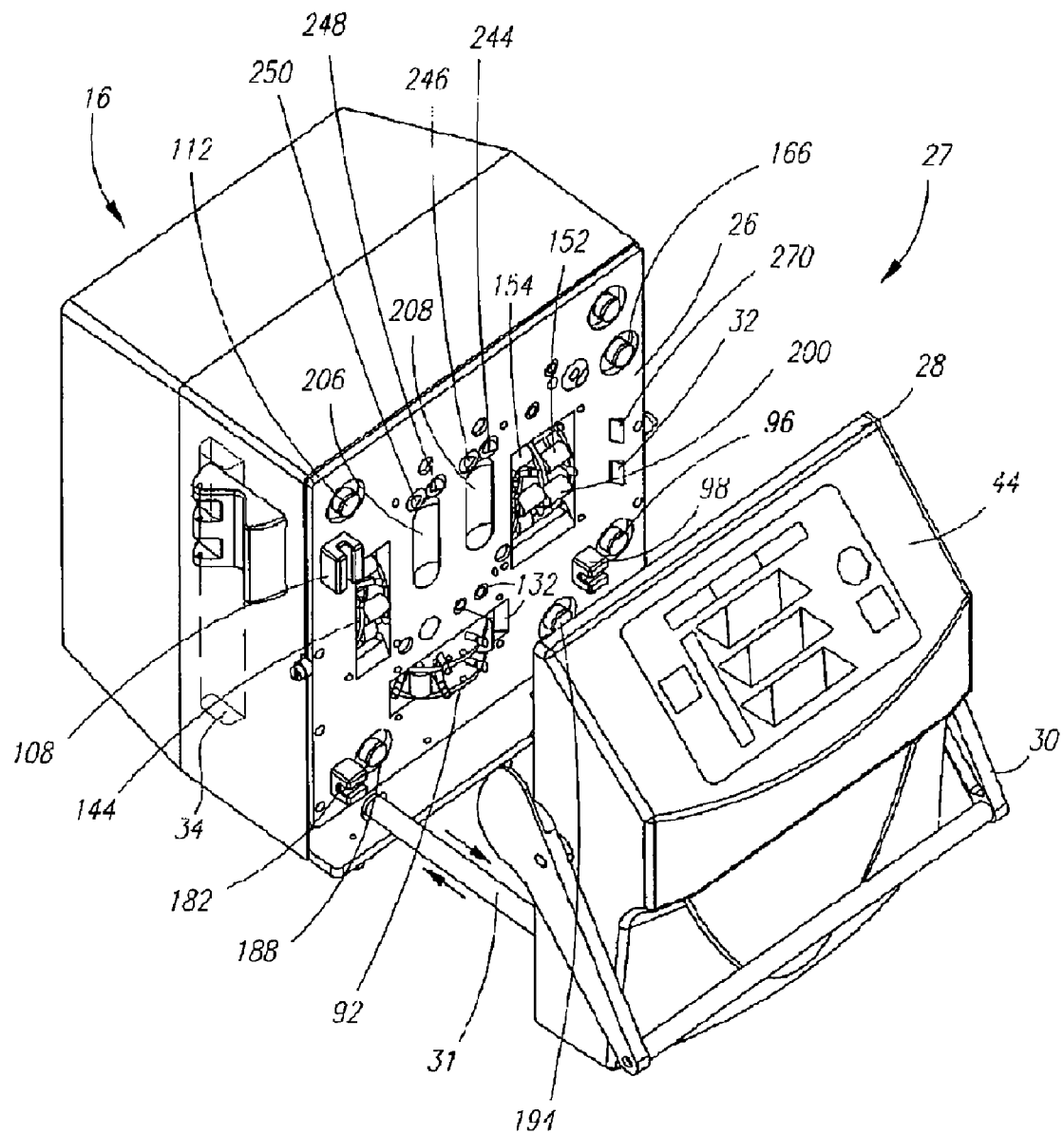
FIG. 2 is a front perspective view of an embodiment of a machine that can form a part of the system shown in FIG. 1.
Figure 19:
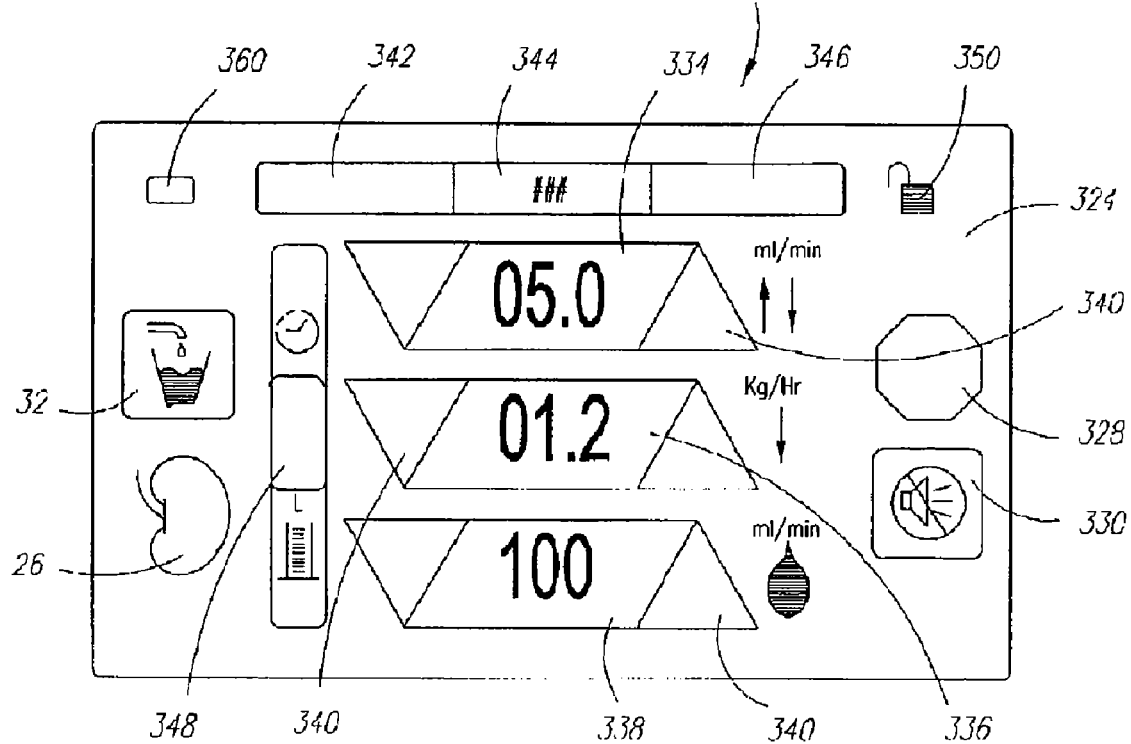
FIG. 19 is a plane view of a graphical user interface that the machine shown in FIG. 2 can incorporate.

Desirably, the machine 16 includes an operator interface 44 (see FIG. 2). FIG. 19 shows a representative display 324 for the operator interface 44 for the machine. The display 324 comprises a graphical user interface (GUI), which, in the illustrated embodiment, is displayed by the interface 44 on the exterior of the door 28, as depicted in FIG. 2. The GUI can be realized, e.g., as a membrane switch panel, using an icon-based touch button membrane. The GUI can also be realized as a "C" language program.

The GUI 324 presents to the operator a simplified information input and output platform, with graphical icons, push buttons, and display bars. The icons, push buttons, and display bars are preferably back-lighted in a purposeful sequence to intuitively lead the operator through set up, execution, and completion of a given treatment session.

B. The Fluid Processing Cartridge

The processing cartridge 18 (see FIG. 3) provides the fluid interface for the machine 16. The fluid interface between the cartridge 18 and machine 16 makes possible a fast and convenient one step process for loading the cartridge 18 for use on the machine 16 (see FIGS. 4 to 6).

In one embodiment, the cartridge 18 establishes a fixed orientation for fluid circuit elements and their operative interface with the hardware elements, such as pumps, sensors, and clamps, on the machine 16. The fixed orientation requires that all safety and control elements on the cartridge 18 and machine 16 are brought into operative association in a single, straightforward loading step. Due to the cartridge 18, the operator cannot place one part of the fluid circuit into an operating condition with one or more hardware elements on the machine 16 without placing the entire fluid circuit into an operating condition with all the hardware elements, including safety systems, on the machine 16.

Desirably, the cartridge 18 makes possible the elimination of air-blood interfaces, and/or positive pressure monitoring. In association with the machine 16, the fluid cartridge 18 can also perform accurate, synchronized volumetric fluid balancing, without the need for weight sensing, as will be described in greater detail later.

The consolidation of all blood and fluid flow paths in a single, easily installed cartridge 18 avoids the potential of contamination, by minimizing the number of connections and disconnections needed during a given treatment session. By enabling a dwell or wait mode on the machine 16, the cartridge 18 can remain mounted to the machine 16 after one treatment session for an extended dwell or break period and allow reconnection and continued use by the same person in a subsequent session for any reason, for example, or in a continuation of a session following x-rays or testing.

The cartridge 18 can therefore provide multiple intermittent treatment sessions during a prescribed time period, without exchange of the cartridge 18 after each treatment session. The time of use confines are typically prescribed by the attending physician or technical staff for the treatment center to avoid bio-contamination and can range, e.g., from 48 hours to 120 hours, and more typically 72 to 80 hours. The cartridge 18 can carry a bacteriostatic agent that can be returned to the patient (e.g., an anticoagulant, saline, ringers lactate, or alcohol) and/or be refrigerated during storage.

The single step loading function can be accomplished in various ways. In the illustrated embodiment (see FIG. 2), the machine 16 includes a chassis panel 26 and a panel door 28. The door 28 moves on a pair of rails 31 in a path toward and away from the chassis panel 26 (as shown by arrows in FIG.

Figure 4:
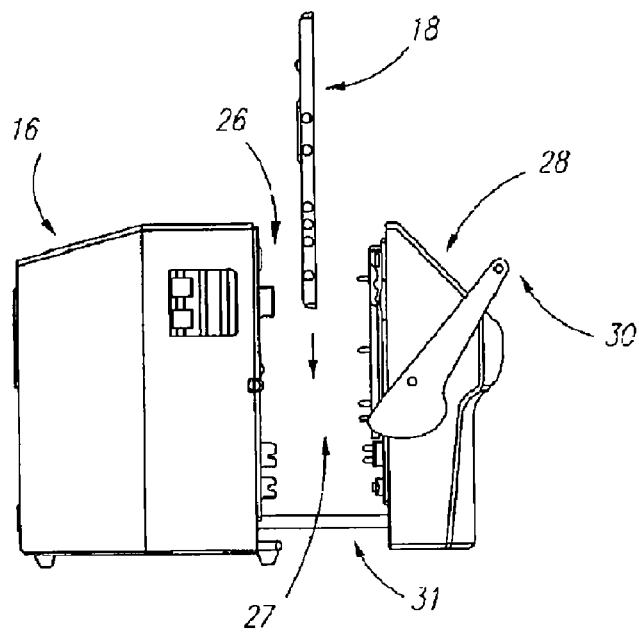
FIGS. 4 to 6 are side elevation views showing the loading of the fluid processing cartridge shown in FIG. 3 onto the machine shown in FIG. 2.
Figure 5:
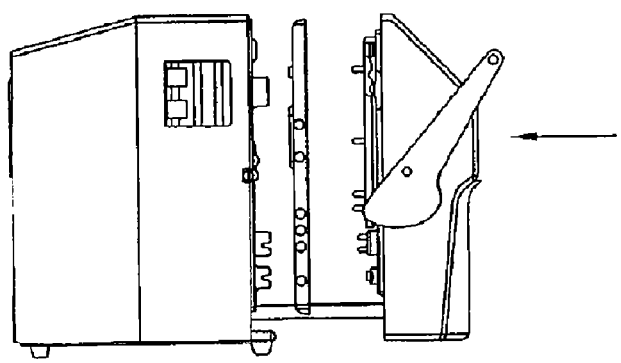
Figure 6:
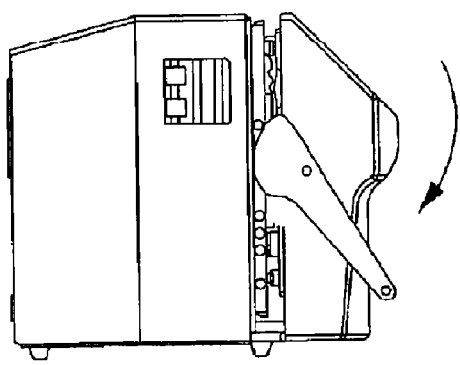

2). A slot 27 is formed between the chassis panel 26 and the door 28. As FIGS. 4 to 6 show, when the door 28 is positioned away from the panel 26, the operator can, in a simple vertical (i.e., downward) motion (see FIG. 4), move a fluid processing cartridge 18 into the slot 27 and, in a simple horizontal (i.e., sideway) motion (see FIG. 5), fit the cartridge 18 onto the chassis panel 26. When properly oriented, the fluid processing cartridge 18 may rest on the rails 31 to help position the cartridge 18. As FIG. 6 shows, movement of the door 28 toward the panel 26 engages and further supports the cartridge 18 for use on the panel 26. This position of the door 28 will be called the closed position.

The machine 16 preferably includes a latching mechanism 30 and a sensor 32 (see FIG. 2) to secure the door 28 and cartridge 18 against movement before enabling circulation of fluid through the cartridge 18.

Figure 3:
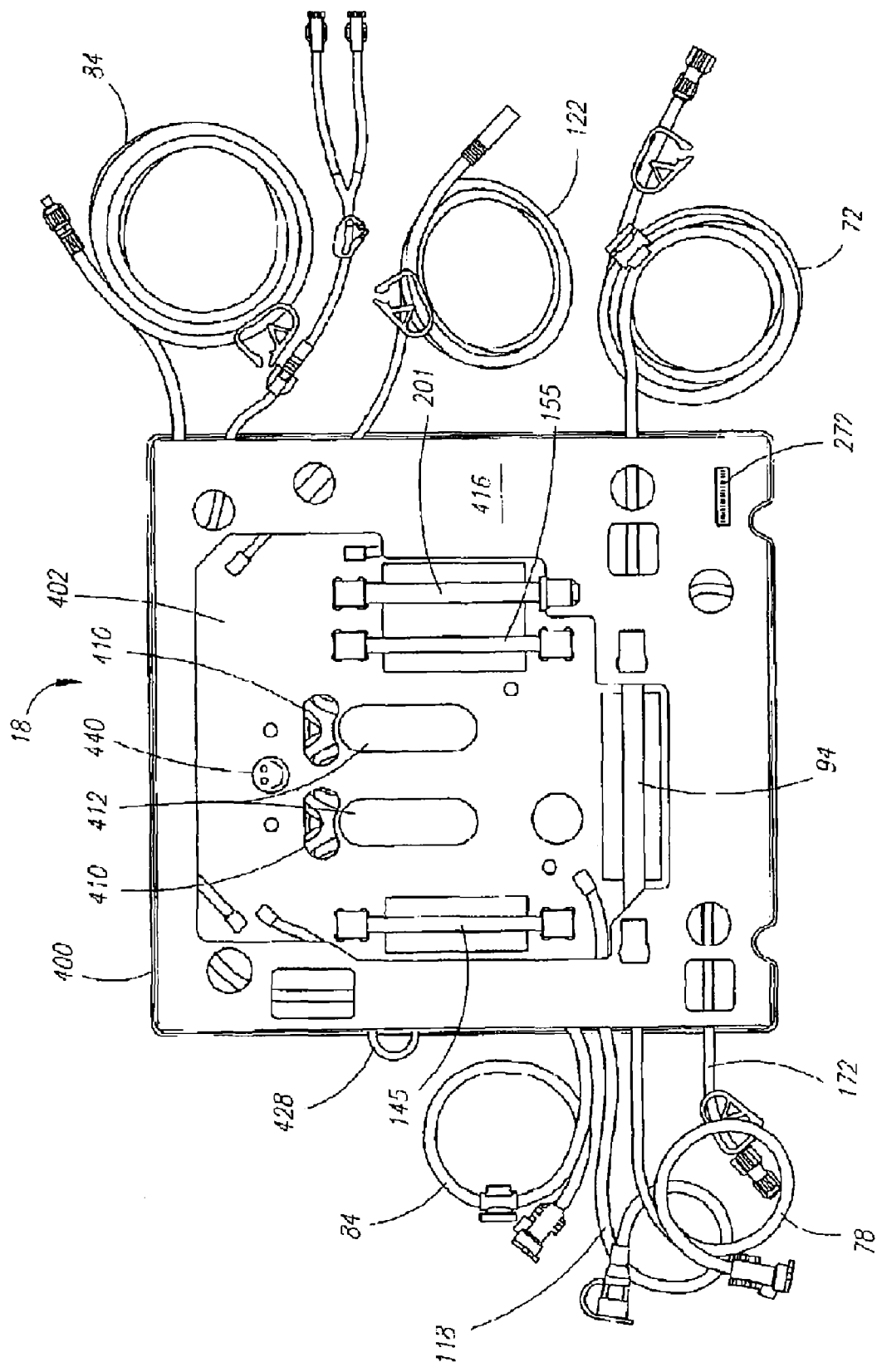
FIG. 3 is a plane view of the exterior surface of an embodiment of a fluid processing cartridge that can form part of the system shown in FIG. 1.

The cartridge 18 can be constructed in various ways. FIG. 3 (in an assembled view) and FIG. 7 (in an exploded view) show an embodiment of a cartridge 18, which can be used to in association with the machine 16 to perform a selected treatment modality. In this embodiment, the cartridge 18 includes a preformed support frame 400 manufactured, e.g., by thermoforming polystyrene or another comparable material. The support frame 400 presents an exterior surface 402 (shown in plane view FIG. 8) and an oppositely facing interior surface 404 (shown in plane view in FIG. 9).

When installed for use on the machine 16, the exterior surface 402 is oriented toward the door 28, and the interior surface 404 is oriented toward the chassis panel 26. An icon 440 imprinted on the exterior surface 402 (see FIG. 8) guides the operator in mounting the frame 400 on the chassis panel 26 in the proper front-to-back and up-and-down orientation.

Figure 7:
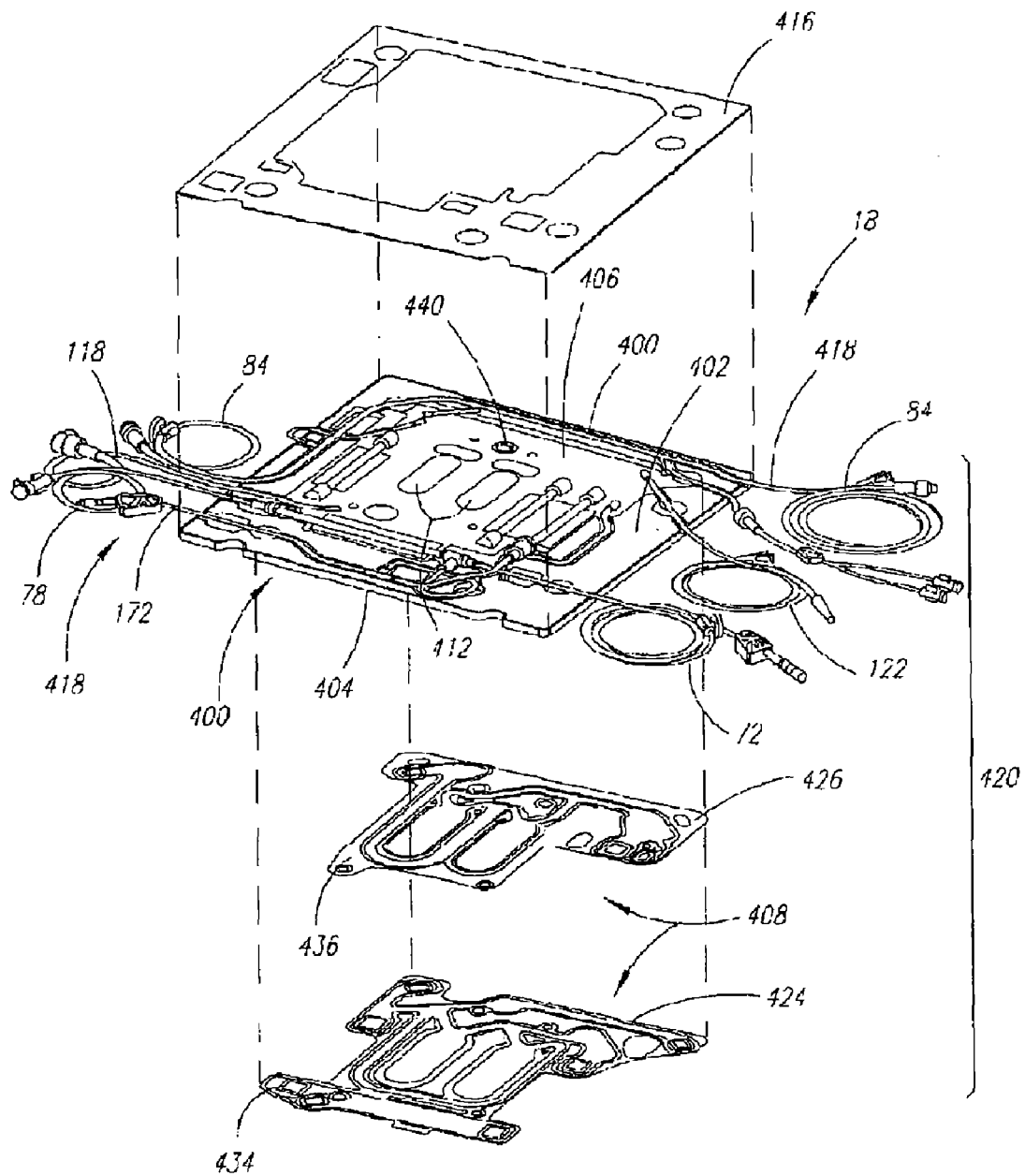
FIG. 7 is a perspective exploded view of the fluid processing cartridge shown in FIG. 3.

As FIG. 7 best shows, the interior surface 404 of the frame 400 carries a flexible fluid circuit 408. In the illustrated embodiment, the flexible fluid circuit 408 comprises one or more individual fluid management modules. The modules can be dedicated to different processing functions. For example, one module can handle fluid being removed from the body, while another module can handle fluid being supplied to the body. These processing functions can be synchronized by various means of orienting the modules with each other, and with the common hardware elements on the machine 16.

Figure 10:
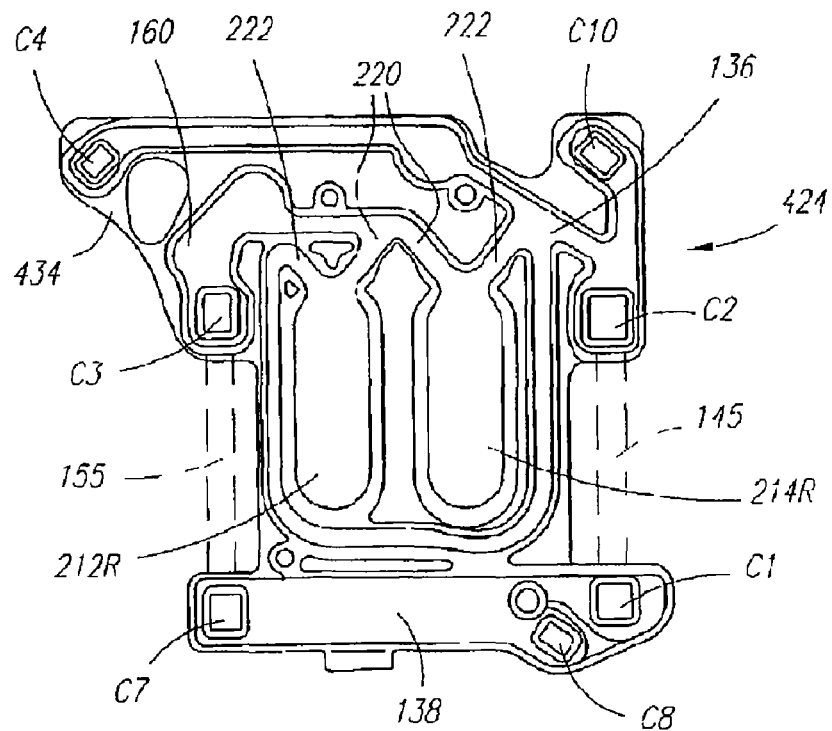
FIGS. 10 and 11 are plane view of fluid management modules that form a part of the fluid circuit carried by the cartridge.
Figure 11:
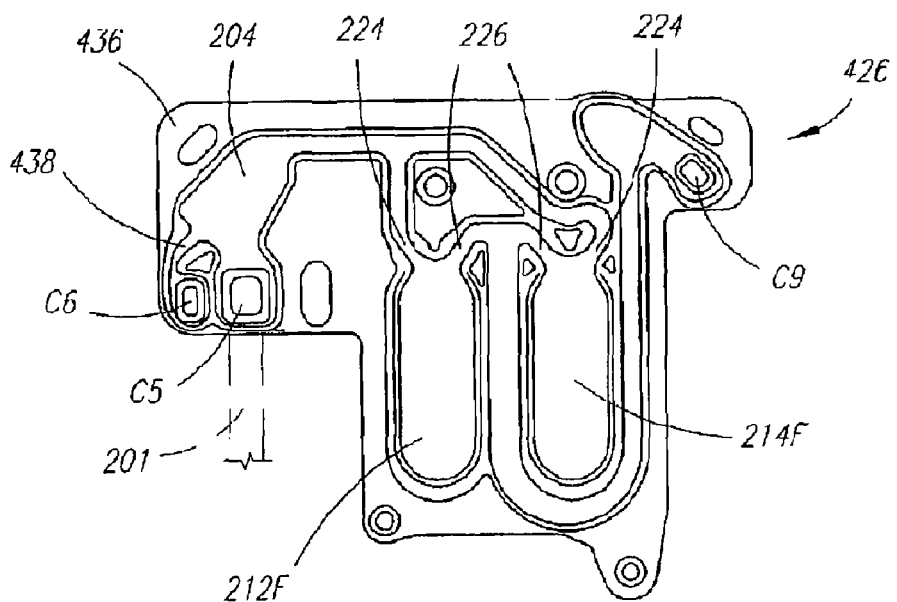

In the illustrated embodiment (see FIG. 7), two modules 424 and 426 are provided, which are shown individually in FIGS. 10 and 11, respectively. As FIG. 7 shows, lengths of flexible tubing 418 communicate with modules 424 and 426 of the flexible fluid circuit 408, to convey fluid to and from the modules 424 and 426. Together, the flexible fluid circuit 408 and tubing 418 form a fluid processing circuit 420.

The modules 424 and 426 themselves can be constructed in various ways, depending upon the particular processing functions that are intended to be performed.

In the illustrated embodiment (see FIGS. 10 and 11), the modules 424 and 426 take the form of fluid circuit bags 434 and 436. Each bag 434 and 436 is formed, e.g., by radio frequency welding together two sheets of medical plastic material (e.g., polyvinyl chloride). Each bag 434 and 436 includes an interior array of radio frequency seals forming fluid paths, chamber regions, sensor regions, and clamp regions.

In the illustrated embodiment, when secured to the interior surface 404 of the frame 400 (see FIGS. 7 and 9), the bag 434 rests over the bag 436, so that portions of the fluid circuits defined by the modules 424 and 426 overlay one another. As will be explained later, this makes possible synchronization of different processing functions using common hardware elements on the machine 16.

II. Telemetry for the System

Figure 18:
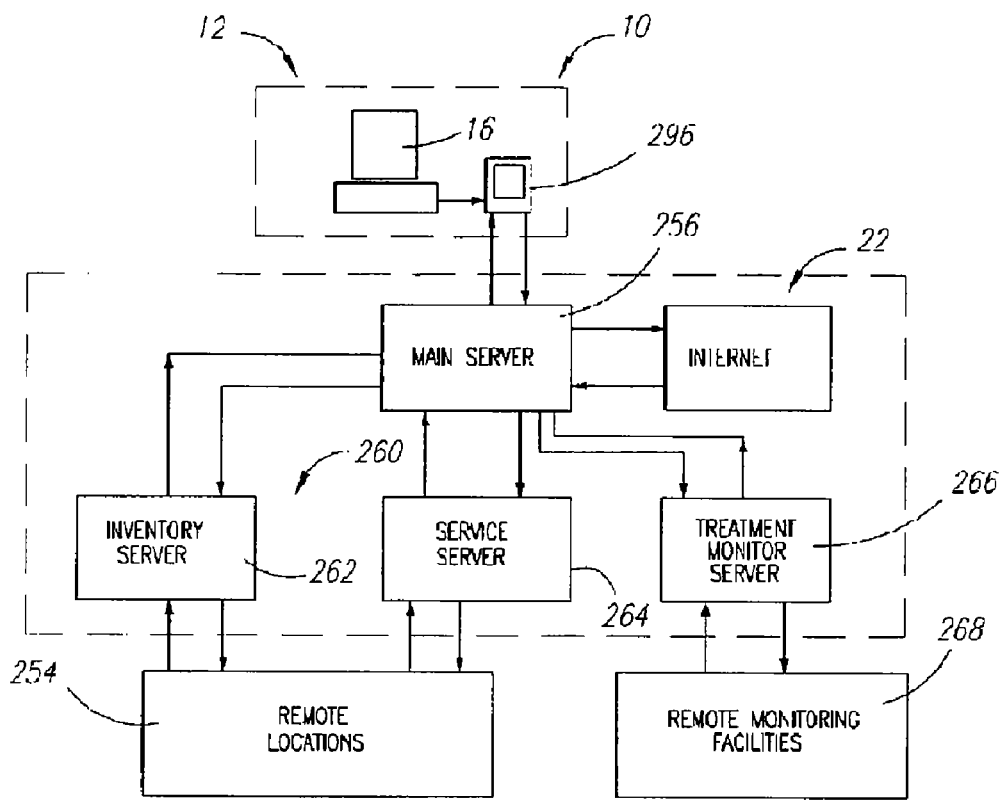
FIG. 18 is a diagrammatic view of a telemetry network that can form a part of the system shown in FIG. 1.

The system 10 can also include a telemetry network 22 (see FIGS. 1 and 18). The telemetry network 22 provides the means to link the machine 16 in communication with other locations 254 via, e.g., cellular networks, digital networks, modem, Internet, or satellites. A given location 254 can, for example, receive data from the machine 16 at the treatment location or transmit data to a data transmission/receiving device 296 at the treatment location, or both. A main server 256 can monitor operation of the machine 16 or therapeutic parameters of the person undergoing the specified treatment. The main server 256 can also provide helpful information to the person undergoing the specified treatment. The telemetry network 22 can download processing or service commands to the data receiver/transmitter 296.

1. Remote Information Management

FIG. 18 shows a representative telemetry network 22 in association with a machine 16 that carries out a specified treatment modality. The telemetry network 22 includes the data receiver/transmitter 296 coupled to the machine 16. The data receiver/transmitter 296 can be electrically isolated from the machine 16, if desired. The telemetry network 22 also includes a main data base server 256 coupled to the data receiver/transmitter 296 and an array of satellite servers 260 linked to the main data base server 256.

The data generated by the machine 16 during operation is processed by the data receiver/transmitter 296. The data is stored, organized, and formatted for transmission to the main data base server 256. The data base server 256 further processes and dispenses the information to the satellite data base servers 260, following pre-programmed rules, defined by job function or use of the information. Data processing to suit the particular needs of the telemetry network 22 can be developed and modified without changing the machine 16.

The main data base server 256 can be located, e.g., at the company that creates or manages the system 10. The satellite data base servers 260 can be located, for example, at the residence of a designated remote care giver for the person, or at a full time remote centralized monitoring facility staffed by medically trained personnel, or at a remote service provider for the machine 16, or at a company that supplies the machine 16 or the processing cartridge 18.

Linked to the telemetry network 22, the machine 16 acts as a satellite. The machine 16 performs specified therapy tasks while monitoring basic safety functions and providing the person at the treatment location notice of safety alarm conditions for resolution. Otherwise, the machine 16 transmits procedure data to the telemetry network 22. The telemetry network 22 relieves the machine 16 from major data processing tasks and related complexity. It is the main data base server 256, remote from the machine 16, that controls the processing and distribution of the data among the telemetry network 22, including the flow of information and data to the person undergoing therapy. The person at the treatment location can access data from the machine 16 through the local data receiver/transmitter 296, which can comprise a laptop computer, handheld PC device, web tablet, cell phone, or any unit capable of data processing.

The machine 16 can transmit data to the receiver/transmitter 296 in various ways, e.g., electrically, by phone lines, optical cable connection, infrared light, or radio frequency, using cordless phone/modem, cellular phone/modem, or cellular satellite phone/modem. The telemetry network 22 may comprise a local, stand-alone network, or be part of the Internet.

For example, when the machine 16 notifies the person at the treatment location of a safety alarm condition, the safety alarm and its underlying data can also be sent to the main server 256 on the telemetry network 22 via the receiver/transmitter 296. When an alarm condition is received by the main server 256, the main server 256 can locate and download to the receiving device 296 the portion of the operator's manual for the machine that pertains to the alarm condition. Based upon this information, and exercising judgment, the operator/user can intervene with operation of the machine 16. In this way, the main server 256 can provide an automatic, context-sensitive help function to the treatment location. The telemetry network 22 obviates the need to provide on-board context-sensitive help programs for each machine 16. The telemetry network 22 centralizes this help function at a single location, i.e., a main server 256 coupled to all machines 16.

The telemetry network 22 can relay to an inventory server 262 supply and usage information of components used for the treatment modality. The server 262 can maintain treatment site-specific inventories of such items, such as cartridges 18, ancillary processing materials, etc. The company or companies that supply the machine 16, the processing cartridge 18, or the ancillary processing material to the treatment location 12 can all be readily linked through the telemetry network 22 to the inventory server 262. The inventory server 262 thereby centralizes inventory control and planning for the entire system 10, based upon information received in real time from each machine 16.

The telemetry network 22 can relay to a service server 264 hardware status information for each machine 16. The service server 264 can process the information according to preprogrammed rules, to generate diagnostic reports, service requests or maintenance schedules. The company or companies of the system 10 that supply or service the machine 16 can all be readily linked through the telemetry network 22 to the service server 264. The service server 264 thereby centralizes service, diagnostic, and maintenance functions for the entire system 10. Service-related information can also be sent to the treatment location 12 via the receiving device 296.

The telemetry network 22 can also relay to a treatment monitoring server 266, treatment-specific information pertaining to the therapy provided by each machine 16. Remote monitoring facilities 268, staffed by medically trained personnel, can be readily linked through the telemetry network 22 to the treatment monitoring server 266, which centralizes treatment monitoring functions for all treatment locations served by the system 10.

The telemetry network 22 can also provide through the device 296 an access portal for the person undergoing treatment to the myriad services and information contained on the Internet, e.g., over the web radio and TV, video, telephone, games, financial management, tax services, grocery ordering, prescriptions purchases, etc. The main server 256 can compile diagnostic, therapeutic, and/or medical information to create a profile for each person served by the system 10 to develop customized content for that person. The main server 256 thus provide customized ancillary services such as on line training, billing, coaching, mentoring, uplinks to doctors, links to patient communities, and otherwise provide a virtual community whereby persons using the system 10 can contact and communicate via the telemetry network 22.

The telemetry network 22 thus provides the unique ability to remotely monitor equipment status, via the internet, then provide information to the user, also via the internet, at the location of the equipment. This information can include, e.g., what page of the operator's manual would be the most helpful for their current operational situation, actual data about the equipment's performance (e.g., could it use service, or is it set up based on the caretaker's recommendations), data about the current session, i.e., buttons pressed, alarms, internal machine parameters, commands, measurements.

The remote site can monitor the equipment for the same reasons that the user might. It can also retrieve information about the machine 16 when it is turned off because the telemetry device is self-powered. It retains all information about the machine over a period of time (much like a flight recorder for an airplane).

2. On-Site Programming

The main server 256 on the telemetry network 22 can also store and download to each machine 16 (via the device 296) the system control logic and programs necessary to perform a desired treatment modality. Programming to alter a treatment protocol to suit the particular needs of a single person at a treatments site can be developed and modified without a service call to change the machine 16 at any treatment location, as is the current practice. System wide modifications and revisions to control logic and programs that condition a machine 16 to perform a given treatment protocol can be developed and implemented without the need to retrofit each machine 16 at all treatment locations by a service call. This approach separates the imparting of control functions that are tailored to particular procedures, which can be downloaded to the machine 16 at time of use, from imparting safety functions that are generic to all procedures, which can be integrated in the machine 16.

Alternatively, the control logic and programs necessary to perform a desired treatment protocol procedure can be carried in a machine readable format on the cartridge 18. Scanners on the machine 16 automatically transfer the control logic and programs to the machine 16 in the act of loading the cartridge 18 on the machine 16. Bar code can be used for this purpose. Touch contact or radio frequency silicon memory devices can also be used. The machine 16 can also include local memory, e.g., flash memory, to download and retain the code.

For example, as FIG. 2 shows, the machine 16 can include one or more code readers 270 on the chassis panel 26. The frame 400 carries, e.g., on a label or labels, a machine readable (e.g., digital) code 272 (see FIG. 3) that contains the control logic and programs necessary to perform a desired treatment protocol using the cartridge 18. Loading the cartridge 18 on the machine 16 orients the code 272 to be scanned by the reader(s) 270. Scanning the code 272 downloads the control logic and programs to memory. The machine 16 is thereby programmed on site.

The code 272 can also include the control logic and programs necessary to monitor use of the cartridge 18. For example, the code 272 can provide unique identification for each cartridge 18. The machine 16 registers the unique identification at the time it scans the code 272. The machine 16 transmits this cartridge 18 identification information to the main server 256 of the telemetry network 22. The telemetry network 22 is able to uniquely track cartridge 18 use by the identification code throughout the system 10.

Furthermore, the main server 256 can include preprogrammed rules that prohibit multiple use of a cartridge 18, or that limit extended uses to a prescribed period of time. An attempted extended use of the same cartridge 18 on any machine 16, or an attempted use beyond the prescribed time period, will be detected by the machine 16 or the main server 256. In this arrangement, the machine 16 is disabled until an unused cartridge 18 is loaded on the machine 16.

Prior to undertaking set up pressure testing and priming of the cartridge 18, the machine 16 can also be conditioned to sense, e.g., by ultrasonic means, the presence of fluid in the cartridge. The presence of fluid indicates a reprocessed cartridge. In this arrangement, the machine 16 is disabled until a dry, unused cartridge 18 is loaded on the machine 16.

Service cartridges can also be provided for the machine 16. A service cartridge carries a code that, when scanned by the reader or readers on the chassis panel 26 and downloaded to memory, programs the machine 16 to conduct a prescribed service and diagnostic protocol using the service cartridge 18.

III. Representative Systems for Conducting Hemofiltration

The particular configuration of the machine 16 and the fluid processing circuit 420, which the tubing 418 and flexible fluid circuit 408 form, can vary according to the processing objectives of the system 10. As before stated, the system 10 is well suited for treatment modalities during which one fluid is removed from the body and replaced with another fluid in a controlled fashion, e.g., hemofiltration (HF), hemodialysis (HD), hemodialysis with hemofiltration (HDF), and peritoneal dialysis (PD).

Figure 12:
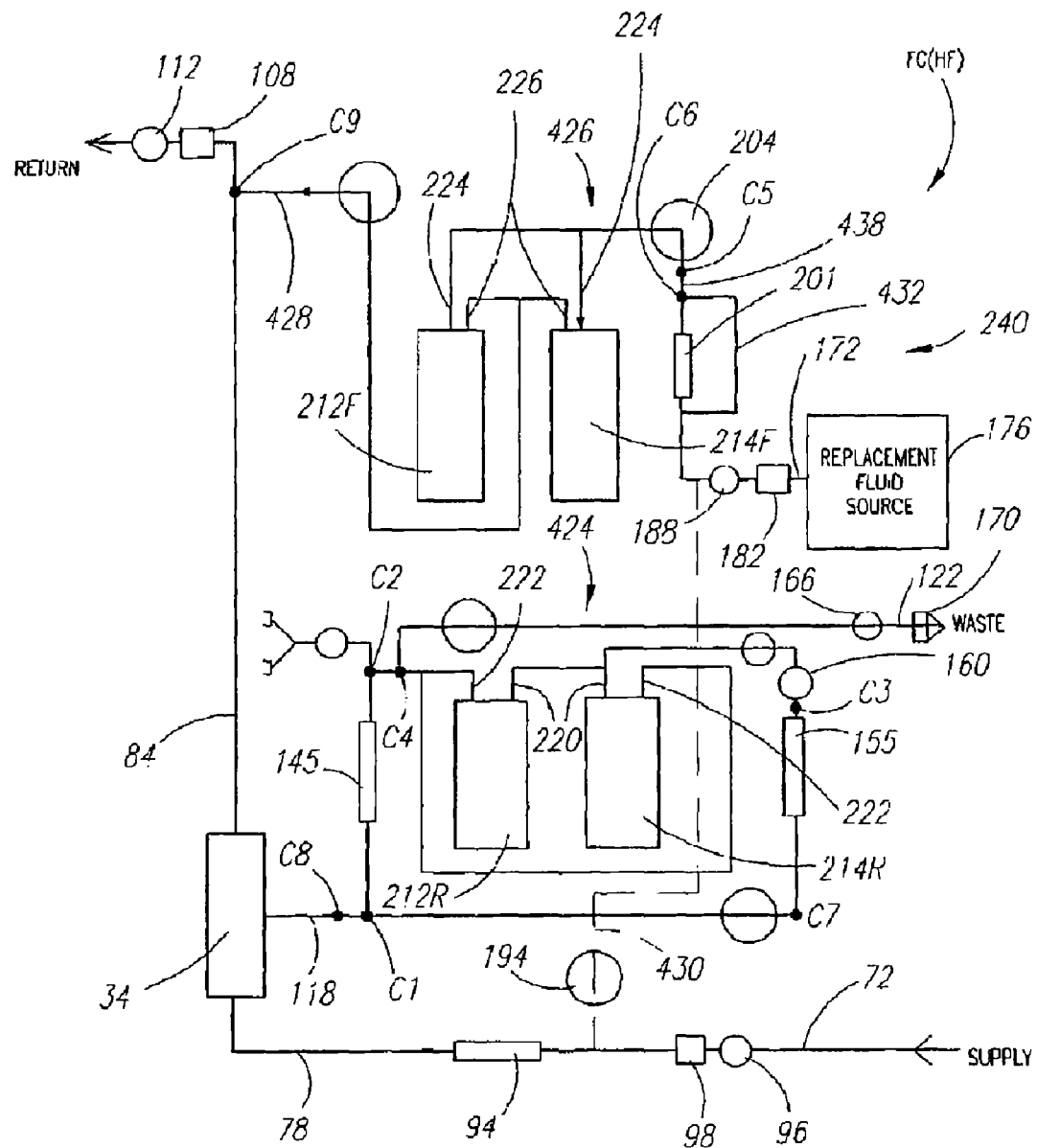
FIG. 12 is a schematic view of a fluid circuit for carrying out hemofiltration, which the cartridge shown in FIG. 3 can be configured to form.

For the purpose of illustration, FIG. 12 schematically shows a fluid circuit FC(HF) for carrying out hemofiltration. The fluid circuit FC(HF) supports the removal of blood from an individual and the separation of waste fluid from the blood using a hemofilter 34. The fluid circuit FC(HF) also supports the return of treated blood and replacement fluid to the individual. The fluid circuit FC(HF) also supports an ultrafiltration function.

The flexible fluid circuit 420 carried by the frame 400 and the machine 16 can be readily configured to form this circuit FC(HF) and thereby conduct hemofiltration. A person of skill in the art will readily appreciate how the fluid circuit 420 and machine 16 can be configured to perform other treatment modalities, as well.

In the illustrated implementation, the first module 424 is configured to handle waste fluid, and the second module 426 is configured to handle replacement fluid.

As FIG. 10 shows, the waste fluid management module 424 includes fluid waste balancing chambers 212R/214R and associated waste fluid clamp regions 220 and 222. The location of these elements in the fluid circuit FC (HF) are also shown schematically in FIG. 12.

As FIG. 11 shows, the replacement fluid management module 426 includes corresponding replacement fluid balancing chambers 212F/214F and associated replacement fluid clamp regions 224 and 226. The location of these elements in the fluid circuit FC(HF) are also shown schematically in FIG. 12.

When the modules 424 and 426 are mounted against the interior surface 404 of the frame 400 (see FIG. 9), the chambers 212R/214R and 212F/214F and the clamp regions 222/220 and 224/226 communicate in the same plane. When the frame 400 is mounted for use on the machine 16, the overlaying chambers 212R/214R and 212F/214F and clamp regions 222/220 and 224/226 operatively engage common machine elements on the machine 16 to carry out volumetric fluid balancing of replacement fluid in proportion to waste removal, without use of weight sensors. When the frame 400 is mounted for use on the machine 16, the modules 424 and 426, in association with hardware elements on the machine 16, also accomplish ultrafiltration.

Figure 13:
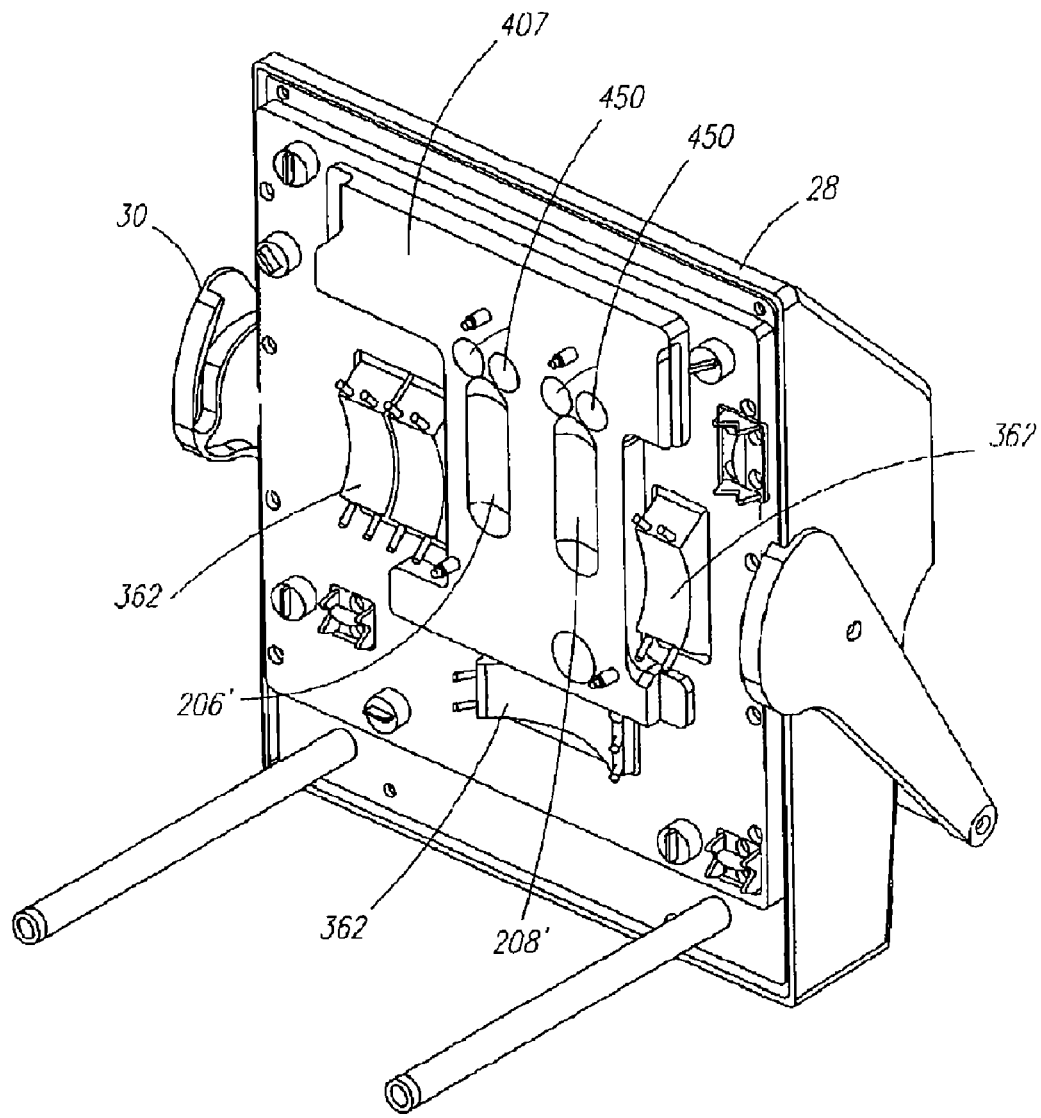
FIG. 13 is a perspective view of the inside of the door of the machine shown in FIG. 2.

In the illustrated embodiment (see FIGS. 7 and 8), an exterior surface 406 of the frame 400 is slightly recessed or concave. When the frame 400 is mounted on the machine 16, this recessed frame surface 406 nests within a correspondingly raised surface 407 on the door 28 (see FIG. 13). When so nested, convex or domed frame regions 412, which project above the surface 406 of the frame 400 (see FIGS. 7 and 8) fit within mating concave indentations 206' and 208' on the door 28.

Figure 8:
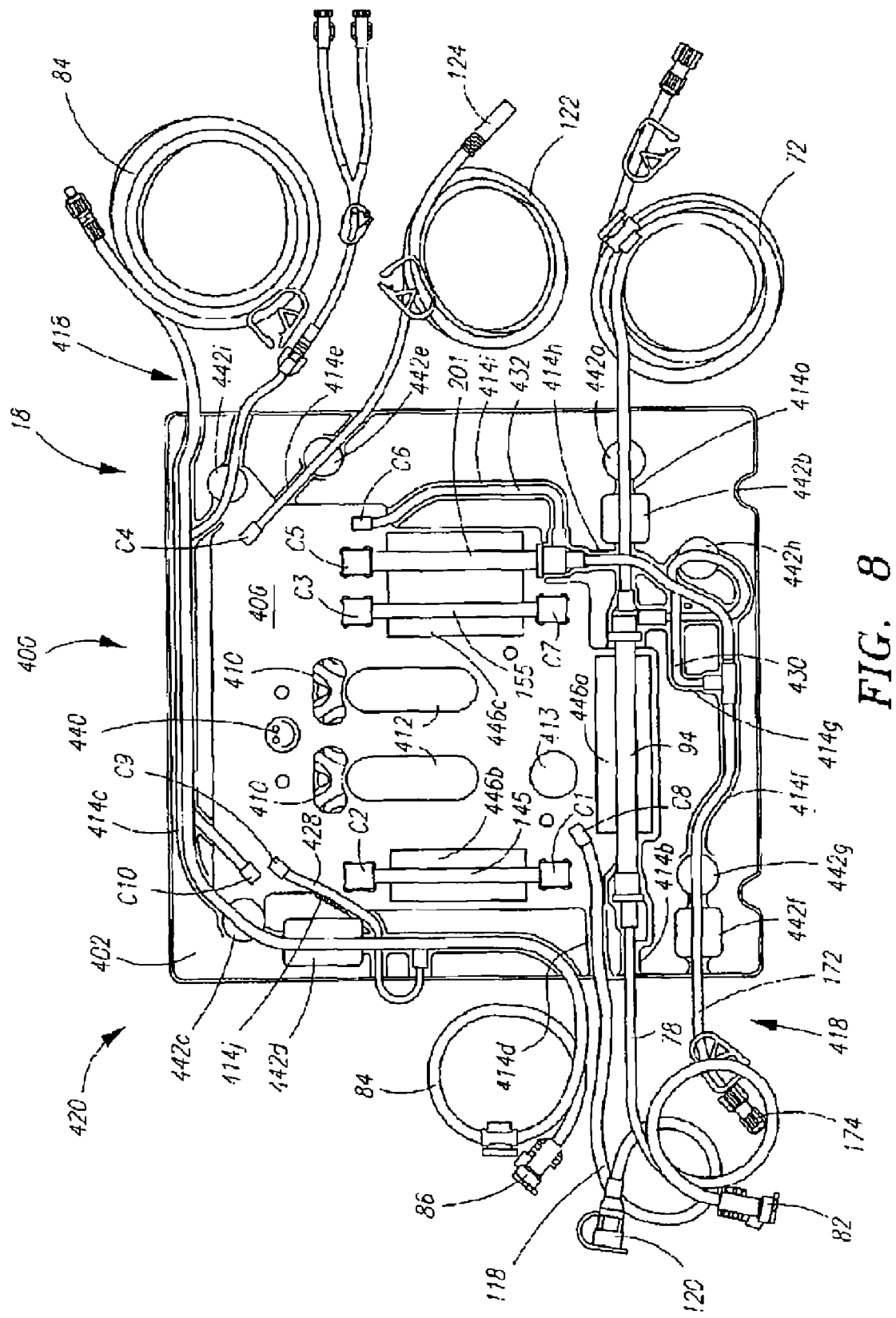
FIG. 8 is a plane view of the exterior surface of the fluid processing cartridge shown in FIG. 3, with the cover member removed to show the channels that guide the passage of flexible tubing that forms a part of the fluid circuit carried by the cartridge.

The fluid balancing chambers 212R/214R and 212F/214F rest in an overlying relationship within these domed regions 412 on the opposite interior surface 404 of the frame 400 (see FIG. 8). When the frame 400 is mounted on the machine 16, and the door 28 closed, the interior surface 404 faces the chassis panel 28, and the fluid balancing chambers 212R/214R and 212F/214F rest within concave indentations 206 and 208 formed on the chassis panel 26 (see FIG. 2). When the frame 400 is mounted on the machine 16, and the door 28 closed, the flexible chambers 212R/214R and 212F/214F are thereby enclosed between the indentations 206/208 on the chassis panel 26 and the convex regions 412 of the frame 400 (which themselves nest within the concave indentations 206'/208' on the door 28). Expansion of the flexible chambers 212R/214R and 212F/214F as a result of fluid introduction is thereby restrained to a known maximum volume, generally approximately between 10 and 50 cc, preferably approximately between 20 and 40 cc, more preferably approximately 25 cc, defined between the chassis chambers 206/208 and the convex frame regions 412.

As FIG. 8 shows, cut-outs 410 in the surface 406 expose the overlaying flexible clamp regions 222/220 and 224/226 to contact with the four clamping pads 450 mounted on the door 28 (see FIG. 13) and hardware clamping elements 244, 246, 248, and 250 on the chassis panel 26 (see FIG. 2). In operation, the clamping elements 244, 246, 248, and 250 are caused to project from the chassis panel 26 to press the overlying clamp regions 222/220 and 224/226 against the clamping pads 450 on the door 28. Synchronized valve functions are thereby made possible, as will be described later.

Referring back to FIG. 8, another cut-out 413 in the surface 406 exposes a portion of the fluid circuit 408 for blood leak sensing functions, as will also be described later.

Surrounding the surface 406 are recessed channel regions 414a to 414j, which are formed in the exterior surface 402. These recessed channel regions 414a to 414j (identified in FIG. 8) accommodate the passage of the lengths of flexible tubing 418 that communicate with the flexible fluid circuit 408, to form the fluid processing circuit 420. The recessed regions 414a to 414j form channels that guide and restrain the tubing 418 within the frame 400. Multiple cut-outs 442a to 442i are formed along the recessed regions 414a to 414j, to expose intervals of the tubing 418 for engagement with clamps or sensors on the machine 16, as will be described.

As FIG. 7 show, a cover member 416 made, e.g., from rigid or semi-rigid paper or plastic, is desirably secured to the exterior surface 402 of the frame 400 to overlay and close the recessed channel regions 414, in which the tubing 418 is carried (FIG. 3 shows the exterior surface 402 with the cover member 416 installed).

As FIG. 8 shows, portions of tubing 418 extend beyond the support frame 400 for connection with the patient and other external items making up the fluid processing circuit 420, as will be described later. Cartridge 18 may extend beyond the edge of machine 16.

Portions of the tubing 418 also communicate with peristaltic pump tubes 94, 145, 155, and 201 located in the surface 406 (see FIG. 8). Cut-outs 446a to 446c are formed in the region 406 beneath the pump tubes 94, 145, 144, and 201, to expose the pump tubes 94, 145, 144, and 201 for engagement with the corresponding peristaltic pump rollers 92, 144, and 152 on the chassis panel 26 (see FIG. 2) and the corresponding pump races 362 on the door 28 (see FIG. 13).

Further regarding the configuration of the fluid processing circuit 420 (see FIG. 8), as adapted to conform to the hemofiltration circuit FC (HF) shown in FIG. 12, the flexible tubing 72 forms the arterial blood supply path, with an appropriate distal connector to couple to an arterial blood access site. The tubing 72 is guided by a recessed channel 414a into the frame 400. Cut-outs 442a and 442b expose the tubing 72 for engagement with an arterial blood line air sensor 98 and arterial blood line clamp 96.

The tubing 72 is coupled with the pump tube 94, which spans the cut-out 446a in the frame 400, for engagement with the blood pump 92 on the chassis panel 26 (see FIG. 2).

Tubing 78 extends from the pump tube region 94 in a recessed channel 414b in the frame 400. The tubing 78 extends beyond the frame 400 and includes the connector 82 to couple the arterial blood path to the inlet of a hemofilter 34 (see FIG. 12).

The placement of the cut-out 442a (and associated air sensor 98 on the machine 16) upstream of the hemofilter 34 allows air bubbles to be detected prior to entering the hemofilter 34. This location is desirable, because, in the hemofilter 34, air bubbles break up into tiny micro-bubbles, which are not as easily detected as bubbles upstream of the hemofilter 34. Placement of the air sensor 98 upstream of the hemofilter 34 also serves the additional purpose of detecting air when the blood pump 92 is operated in reverse, to rinse back blood to the patient. The air sensor 98 also detects if the arterial blood line is clamped or otherwise occluded, to thereby allow terminate operation of the arterial blood pump 92 when this condition occurs. Air sensor 98 can also sense a clamped or occluded arterial line while the pump turns. The resulting negative pressure degasses the blood which is sensed by the air sensor, and an alarm is sounded. If air by chance enters the arterial blood line, e.g., by a faulty connection or an air leak, the air sensor 98 will detect this condition and terminate operation of the arterial blood pump before the air enters the hemofilter.

As FIG. 8 shows, the tubing 84 extends beyond the frame 400 and includes a distal connector 86 to couple to the blood outlet of the hemofilter 34 (see FIG. 12). The tubing 84 is led across the frame 400 through a recessed channel 414c. Cut-away regions 442c and 442d on the frame 400 expose the tubing 84 for engagement with the venous blood line air sensor 108 and venous S blood line clamp 112 (see FIG. 12). The tubing 84 then extends beyond the frame 400, and carries an appropriate distal connector to couple to venous blood access site.

As FIG. 8 shows, the flexible tubing 118 extends beyond the frame 400 and carries a distal connector 120 to couple to the waste outlet of the hemofilter 34 (see FIG. 12). The tubing 118 thereby serves to convey waste fluid for fluid balancing and discharge. The flexible tubing 118 enters a recessed channel 414d in the frame 400 and joins a connector C8. The connector C8 couples the tubing 118 to the waste fluid management module 424, and through the module 424 to ultrafiltration pump tube 145 (through connector C1) and the waste pump tube 155 (through connector C7). The pump tube 145 spans a cut-out 446c in the frame 400 to connector C2, for engagement with the ultrafiltration pump 144 on the chassis panel 26 (see FIG. 2). The pump tube 155 spans a cut away region 446d in the frame 400 to connector C3, for engagement with the waste fluid header region 154 of the dual header waste and replacement pump 152 on the chassis panel 26 (see FIG. 2).

Connectors C2 and C3 are fluidically coupled via the waste fluid management module 424 (see FIG. 10) to connectors C10 and C4. As FIG. 8 shows, the flexible tubing 122 is coupled by the connector C4 to an outlet of the waste management module 424. The tubing 122 is guided through a recessed channel 414e in the support frame 400. Cut-away region 442e on the frame 400 expose the tubing 122 for engagement with the waste line clamp 166. The tubing 122 then extends beyond the frame 400, with an appropriate distal connector 124 to couple to a waste bag or an external drain. It is through this tubing 122 that waste fluid is discharged after fluid balancing. An in-line air break 170 (see FIG. 12) can be provided in communication with the tubing 122 downstream of the waste clamp 166, to prevent back flow of contaminants from the waste bag or drain.

Referring to FIG. 8, the flexible tubing 172 serves to convey replacement fluid. The tubing 172 extends outside the frame 400 and includes a distal connector 174 that enables connection to multiple containers of replacement fluid 176 (see FIG. 12). The tubing 172 is guided by a recessed channel 414f within the frame 400. Cut-away regions 442f and 442g on the frame 400 expose the tubing 172 for engagement with an in line air sensor 182 and replacement fluid clamp 188 (see FIG. 12).

Flexible tubing 430 is guided through a recessed channel 414g in the support frame 400 between two t-connectors, one in the arterial blood tubing 72 and the other in the replacement tubing 172. The tubing 430 serves as the priming or bolus branch path 192, as will be described. A cut-away region 442h on the frame 400 exposes the tubing 430 for engagement with the priming clamp 194 on the machine 16 (see FIG. 12).

The replacement fluid tubing 172 is further guided by the recessed channel 414h in the frame 400 to the replacement fluid pump tube 201 (previously described), which is also coupled via a connector C5 to the replacement fluid management module 426 of the flexible fluid circuit 408. As FIG. 11 also shows, connector C5 is also fluidically coupled via the replacement fluid management module 426 to the connectors C6 and C9. The pump tube 201 spans the cut away region 446d in the frame 400, for engagement with the replacement fluid header region 200 of the dual header waste and replacement pump 152 on the chassis panel 26 (see FIG. 2).

Flexible tubing 432 is coupled by a connector C6 to the replacement fluid module 426. The flexible tubing 432 is guided through a recessed channel 414i in the support frame to a t-connector, which joins the replacement tubing 172 in the region immediately downstream of the connection with the replacement fluid pump tube 201. The tubing 432 serves as the relief path 240 that prevents overfilling of the fluid balancing compartments, as will be described.

Flexible tubing 428 is coupled by a connector C9 to the replacement fluid management module 426. The tubing 428 is guided through a recessed channel 414j in the support frame 400 in a small loop outside the frame 400 and is coupled by a t-connector to the venous blood return tubing 84. It is through this path that replacement fluid is added to the venous blood being returned to the patient.

The bags 434 and 436 are secured in overlaying alignment to the interior surface 404 of the frame 400 by the connectors C1 to C10, previously described.

Figure 9:
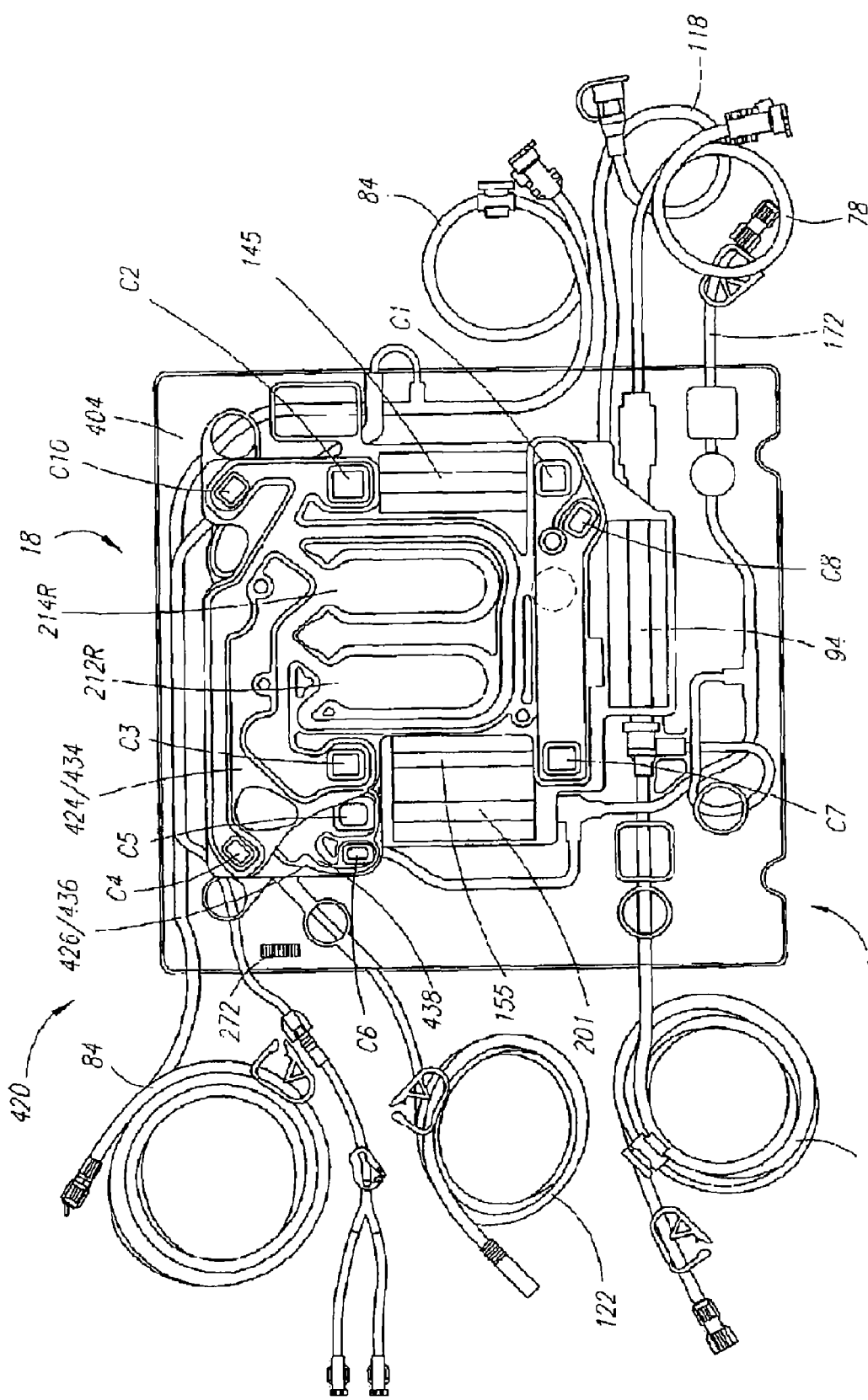
FIG. 9 is a plane view of the interior surface of the fluid processing cartridge shown in FIG. 3.

FIG. 10 shows the waste management fluid circuit contained in the bag 434, as it would appear if viewed from interior surface 404 of the support frame 400 (as FIG. 9 also shows). The bag 434 is shown in association with the ultrafiltration pump tube 145 and waste fluid pump tube 155 that are also carried on the region 406 of the support frame 400.

The fluid circuit in the bag 434 includes the waste path 138 that leads to the waste side compartments 212R and 214R (for fluid balancing) by way of the waste pump 155 and the waste path 136 by way of the ultrafiltration pump 145 that bypasses the waste side compartments 212R and 214R (for ultrafiltration). The flow paths in the waste fluid circuit in the bag 434 also include the exposed waste inlet clamp regions 220, to engage the valve assemblies 246 and 248 to control inflow of waste fluid into the waste compartments 212R and 214R, and the exposed waste outlet clamp regions 222, to engage the valve assemblies 244 and 250 to control outflow of waste fluid from the waste compartments 212R and 214R. The fluid circuit also includes the pressure sensor region 160, to engage the pressure sensor 156 (see FIG. 15) downstream of the waste and replacement fluid pump 152.

FIG. 11 shows the replacement fluid management circuit contained in the bag 436, as it would appear if viewed from the interior surface 404 of the support frame 400 (as FIG. 8 also shows). The bag 436 is shown in association with the replacement fluid pump tube 201 that is also carried in the region 406 of the support frame 400. The replacement fluid pump tube 201 is located alongside the waste fluid pump tube 155, on region 200 for concurrent engagement with the dual header waste and replacement pump 152 on the chassis panel 26 (see FIG. 2).

The fluid circuit in the bag 436 includes the replacement fluid paths which lead to and from the replacement side compartments 212F and 214F. The fluid circuit also includes the inlet clamp regions 224, to engage the valve assemblies 244 and 250 on the machine 16 to control inflow of replacement fluid into the replacement side compartments 212F and 214F; and the outlet clamp regions 226, to engage the valve assemblies 246 and 248 on the machine 16 to control outflow of replacement fluid from the replacement side compartments 212F and 214F. The fluid circuit includes a sensor region 204, to engage the pressure sensor 202 (see FIG. 15) downstream of the waste and replacement pump 152.

When the bags 434 and 436 are mounted in overlaying relationship on the interior frame surface 404 (as FIG. 9 shows), the replacement side compartments 212F and 214F and the waste side compartments 212R and 214R together rest in the convex recesses 412 in the region 406 of the exterior frame surface 402. The inlet clamp regions of the waste compartments 212R and 214R formed on the waste panel 234 overlay the outlet clamp regions of the replacement compartments 212F and 214F formed on the replacement panel 232, and vice versa.

The entry and exit paths serving the waste and replacement compartments formed in the bags 434 and 436 (shown in FIG. 9) are all located at the top of the chambers 212R, 214R, 212F, and 214F. Priming is achieved, as the paths are top-oriented. Furthermore, due to the overlaying relationship of bags 434 and 436, the clamping regions 220, 222, 224, and 226 are arranged to overlay one another. The overlaying arrangement of the clamping regions 220, 222, 224, and 226 serving the waste and replacement compartments simplifies the number and operation of the inlet and outlet valve assemblies 216 and 218 on the machine 16. Since the inlet clamp regions 224 for the replacement compartments 212F and 214F overlay the outlet clamp regions 222 for the waste compartments 212R and 214R, and vice versa, only four clamping elements 244, 246, 248, 250 need be employed to simultaneously open and close the overlaying eight clamp regions.

1. Achieving Synchronized Volumetric Fluid Balancing

Figure 14:
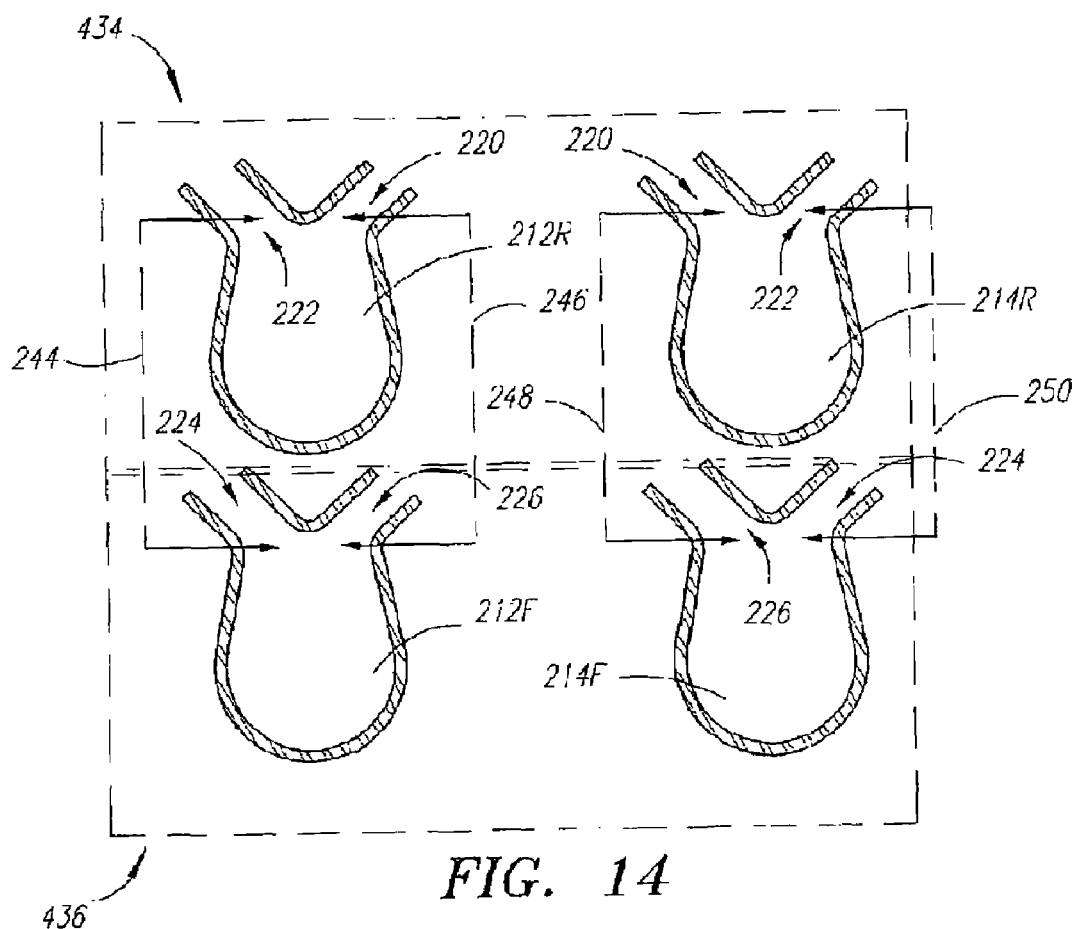
FIG. 14 is a largely schematic side section view of the overlaying fluid balancing compartments that are part of the fluid management modules shown in FIGS. 10 and 11, showing their orientation with valve elements carried by on the machine shown in FIG. 2.

In use, as FIG. 14 shows, the first clamping element 244 is movable into simultaneous clamping engagement with the inlet clamp region 224 of the replacement compartment 212F (in the replacement fluid module bag 436) and the outlet clamp region 222 of the waste compartment 212R (in the waste fluid module bag 434), closing both. Likewise, the fourth clamping element 250 is movable into simultaneous clamping engagement with the inlet clamp region 224 of the replacement compartment 214F (in the replacement fluid module bag 436) and the outlet clamp region 222 of the waste compartment 214R (in the waste fluid module bag 434).

The second clamping element 246 is movable into simultaneous clamping engagement with the outlet clamp region 226 of the replacement compartment 212F and the inlet clamp region 220 of the waste compartment 212R, closing both. Likewise, the third clamping element 248 is movable into simultaneous clamping engagement with the outlet clamp region 226 of the replacement compartment 214F and the inlet clamp region 220 of the waste compartment 214R, closing both.

The machine 16 toggles operation of the first and third clamping elements 244, 248 in tandem, while toggling operation the second and fourth clamping elements 246, 250 in tandem. When the first and third clamping elements 244, 248 are operated to close their respective clamp regions, replacement fluid enters the replacement compartment 214F to displace waste fluid from the underlying waste compartment 214R, while waste fluid enters the waste compartment 212R to displace replacement fluid from the overlaying replacement compartment 212F. When the second and fourth clamping elements 246, 250 are operated to close their respective clamp regions, replacement fluid enters the replacement compartment 212F to displace waste fluid from the underlying waste compartment 212R, while waste fluid enters the waste compartment 214R to displace replacement fluid from the overlaying replacement compartment 214F.

Figure 15:
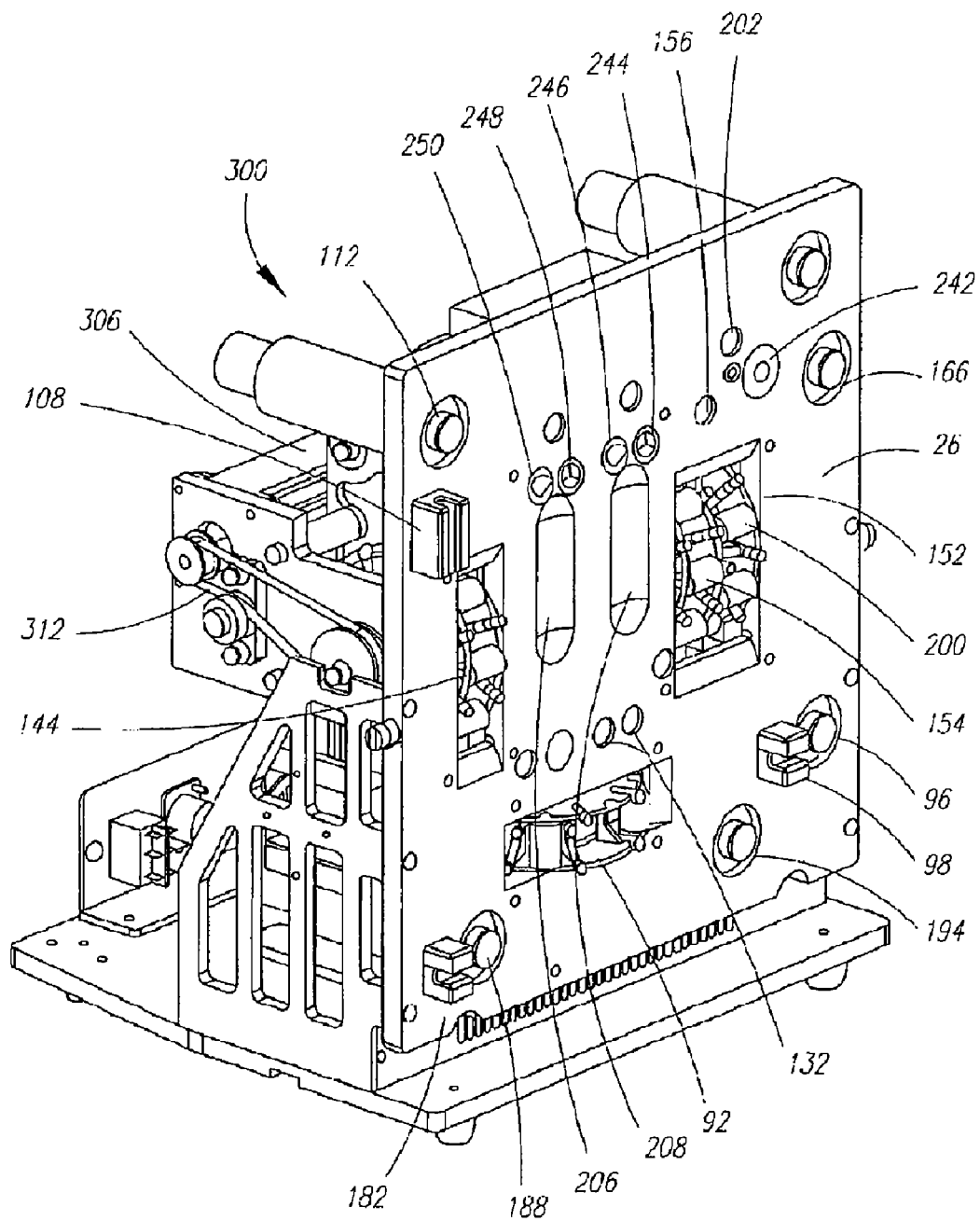
FIG. 15 is a front perspective view of an embodiment of a chassis panel that the machine shown in FIG. 2 can incorporate.
Figure 16:
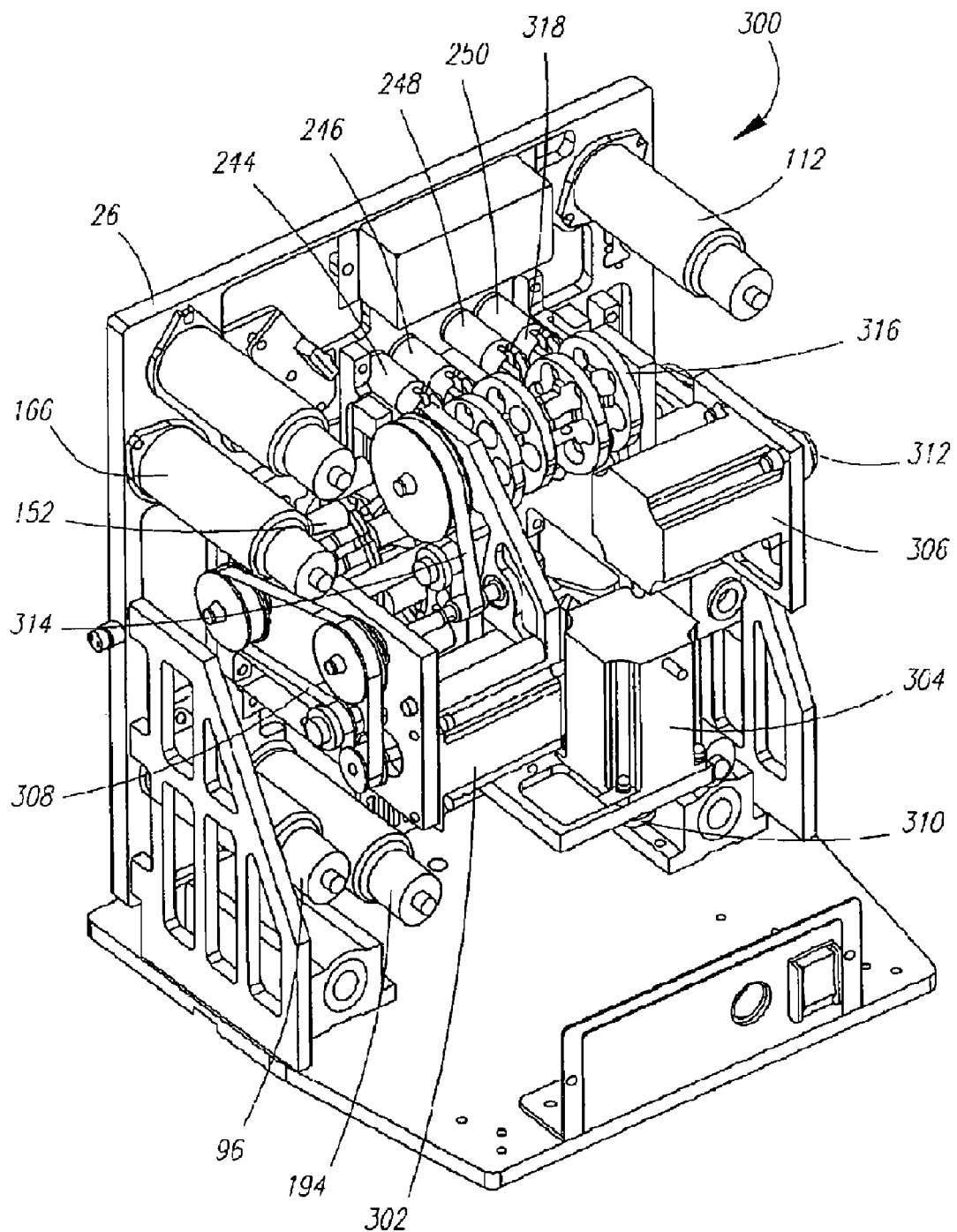
FIG. 16 is a back perspective view of the chassis panel shown in FIG. 15, showing the mechanical linkage of motors, pumps, and valve elements carried by the chassis panel.

FIGS. 15 and 16 show a mechanically linked pump and valve system 300 that can be arranged on the chassis panel 26 of the machine 16 and used in association with the flexible fluid circuit 408.

The system 300 includes three electric motors 302, 304, and 306. The first motor 302 is mechanically linked by a drive belt 308 to a dual header waste and replacement pump 152. The second motor 304 is mechanically linked by a drive belt 310 to a blood pump 92. The third motor 306 is mechanically linked by a drive belt 312 to an ultrafiltration pump 144.

A drive belt 314 also mechanically links the first motor to the first, second, third, and fourth clamping elements 244, 246, 248, and 250, via a cam actuator mechanism 316. The cam actuator mechanism 316 includes, for each clamping element 244, 246, 248, and 250 a pinch valve 318 mechanically coupled to a cam 320. The cams 320 rotate about a drive shaft 322, which is coupled to the drive belt 314.

Rotation of the cams 320 advances or withdraws the pinch valves 318, according to the surface contour machined on the periphery of the cam 320. When advanced, the pinch valve 318 closes the overlying clamp regions of the fluid circuit module bags 424 and 426 that lay in its path. When withdrawn, the pinch valve 318 opens the overlying clamp regions.

The cams 320 are arranged along the drive shaft 322 to achieve a predetermined sequence of pinch valve operation. During the sequence, the rotating cams 320 first simultaneously close all the clamping elements 244, 246, 248, and 250 for a predetermined short time period, and then open clamping elements 244 and 248, while closing clamping elements 246 and 250 for a predetermined time period. The rotating cams 320 then return all the clamping elements 244, 246, 248, and 250 to a simultaneously closed condition for a short predetermined time period, and then open clamping elements 246 and 250, while closing clamping elements 244 and 248 for a predetermined time period.

The sequence is repeated and achieves the balanced cycling of replacement fluid and waste fluid through the module bags 424 and 426, as previously described. A chamber cycle occurs in the time interval that the valve elements 244, 246, 248, and 250 change from a simultaneously closed condition and return to the simultaneously closed condition.

Figure 17:
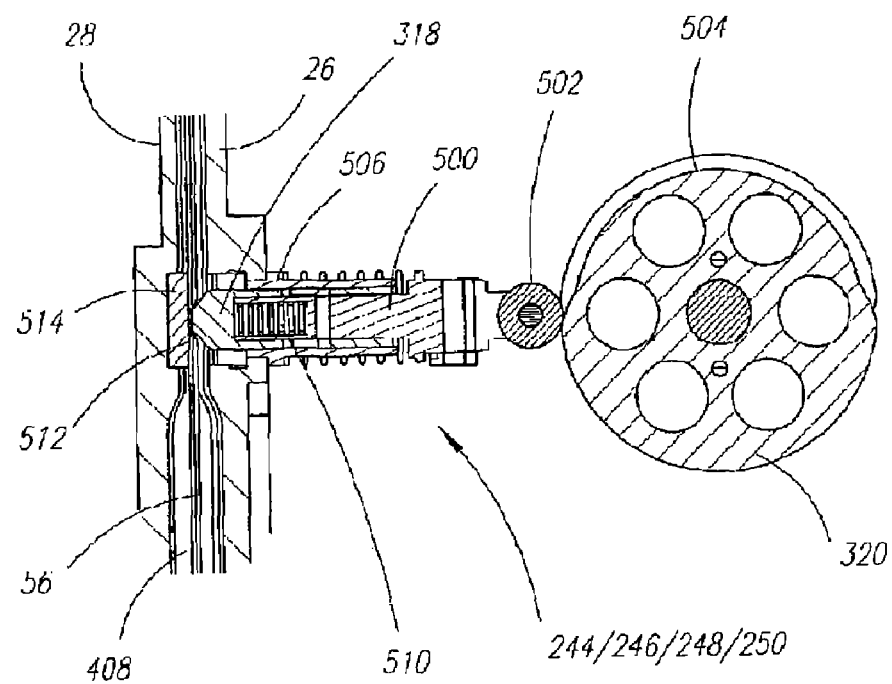
FIG. 17 is a side section view of one of the clamp elements shown in FIGS. 15 and 16.

In a preferred embodiment (see FIG. 17), each clamping element 244, 246, 248, and 250 comprises a valve pin 500 movable within a valve slot 506 in the chassis panel 26. A rotating bearing surface 502 at one end of the valve pin 500 rides on the cam surface 504 of the corresponding rotating cam 320. As the cam 320 rotates, the cam surface 504 presents regions of increasing or decreasing radius, causing the pin 500 to reciprocate within the valve slot 506 toward and away from the door 28, which, during use of the fluid circuit 408, faces the chassis panel 26 in the closed position.

A pinch valve 318 is carried at the opposite end of the valve pin 500. The pinch valve 318 includes a pinch valve chamber 508, in which the valve pin 500 rests. A spring 510 in the pinch valve chamber 508 couples the pinch valve 318 to the valve pin 500. The spring 510 applies a fixed valve force against the pinch valve 318, in the absence of physical contact between the end of the valve pin 500 and the pinch valve 318. The spring 510 thereby mediates against over- and under-valving effects as a result of small changes in tolerance between the pin 500 and pinch valve 318, fluid circuit module bag 424 and 426 thickness, and the closed gap between door 28 and chassis 26.

When mounted for use on the chassis panel 26, with the door 28 closed, the fluid circuit 408 is sandwiched between the panel 26 and the door 28. Each pinch valve 318 is aligned with a valve plate 512 carried by the door 28. The valve plate 512 is made from a hard plastic or metallic material. The valve plate 512 rests against a disk 514 on the door 28, which can be made of rubber or another elastomeric material. The disk 514, which can also be a spring, allows the valve plate 512 to move or "float" when the pinch valve applies a valve force. The valve plate 512 thereby accounts for any lack of perpendicularity between the pinch valve 318 and the valve plate 512.

Movement of the pinch valve 318 toward the door 28 (as the cam surface 504 presents regions of increasing radius) pinches the intermediate, aligned clamp region in the fluid circuit 56 (comprised of modules 424 and 426 overlying one another) between the pinch valve 318 and the valve plate 512, thereby closing the valve region. Likewise, movement of the pinch valve 318 toward the door 28 (as the cam surface 504 presents regions of decreasing radius) separates the pinch valve 318 from the valve plate 514, thereby opening the intermediate valve region. The cam actuator mechanism 316 mechanically links the clamping elements 244, 246, 248, and 250 ratiometrically with the first motor 302. As the motor 302 increases or decreases the speed of the dual header waste and replacement pump 152, the operation of the clamping elements 244, 246, 248 and 250 increases or decreases a proportional amount.

In a preferred embodiment, the ratio is set so that the flow rate per unit time through the waste pump header region 154 (i.e., through waste path 434) approximately equals three-fourths of the volume of the waste compartment 212R/214R, while maintaining the cycle rate of 10 cycles per minute for a waste fluid flow rate of approximately 200 ml/min. For example, if the chamber volume is 25 cc, the cycle occurs after 18 to 21 cc of waste fluid enters the compartment. In other embodiments, the cycle rate is 9-11 cycles per minute for a waste fluid flow rate of approximately 180-220 ml/min, or the cycle rate is 8-12 cycles per minute for a waste fluid flow rate of approximately 160-240 ml/min.

In the illustrated embodiment, the waste pump header 155 is made smaller in diameter than the replacement fluid header 201. Thus, during operation of the dual header pump 152, which is made up of pump regions 154 and 200, the flow rate through the replacement fluid header region 200/201 (through replacement fluid path 426) will always be larger than the flow rate through the waste pump header region 154/155 (through waste path 424). Due to the higher flow rate through the replacement fluid path 426, a pressure relief path 438 (see FIG. 11) and 432 (see FIGS. 12 and 8) with pressure relief bypass valve 242 (see FIG. 15) is provided, to prevent overfilling. In the illustrated embodiment, the valve 242 is a mechanically spring biased pressure regulator, and serves the pressure regulation and bypass function of the machine 16.

In this arrangement, the in-line compartment that receives waste fluid will fill to approximately three-fourths of its volume during each cycle, displacing an equal amount of replacement fluid from its companion compartment. At the same time, the other in-line compartment that receives replacement fluid will fill completely. If the compartment completely fills with replacement fluid before the end of the cycle, the pressure relief bypass valve 242 (see FIG. 15) will open to circulate replacement fluid through the relief path 240, made up of 438, C6, and 432 (see FIG. 12), to prevent overfilling. During the next cycle, waste fluid in the compartment will be completely displaced by the complete fill of replacement fluid in its companion compartment.

The provision of a higher flow rate in the replacement fluid path also facilitates initial priming (as will be described later) only several chamber cycles are required to completely prime the in-line containers 212 and 214 with replacement fluid before fluid balancing operations begin.

The pump and valve system 300 used in association with the fluid circuit 408 achieves accurate fluid balancing, e.g., during hemofiltration, hemodialysis, hemodialysis with hemofiltration, and peritoneal dialysis.

B. Fluid Flow Path Dimensions

In one embodiment, key functional regions within the flexible fluid circuits are formed to possess dimensions that lay within critical ranges, to thereby achieve desired fluid flow conditions, pressure sensing conditions, fluid balancing functions, and valve functions. For example, each fluid balancing chamber 212 F/R and 214 F/R is formed to have a height (measured between the bottom of the chamber and the clamp regions) of between about 3.25 inches and about 5.0 inches, with a nominal height of about 3.6 inches. In this embodiment, each fluid balancing chamber 212 F/R and 214 F/R is formed to have a width (measured between the sides of the chamber and determined by the width of pinch clamp 318) of between about 1.0 inch and about 2.75 inches, with a nominal width of about 1.2 inches. These dimensions help optimize volumetric fluid balance functions.

Further, in another embodiment, each clamp region 220/222 and 224/226 is formed to have a channel width of between about 0.10 inch and 0.40 inch. Bead suppression measures are employed in the clamp regions 220/222 and 224/226 to keep the material adjacent the welded seams, which form the clamp regions, from exceeding more than twice the thickness of the material walls. These steps assure reliable functioning of the overlaying clamp regions in association with the external clamps.

Also, in another embodiment, the ultrafiltration fluid path 136 is formed to have a channel width of greater than about 0.140 inch but less than about 0.60 inch. This optimizes the flow of waste fluid.

In a preferred embodiment, the regions where pressure is sensed in the fluid circuit is formed to have in an interior diameter that is greater than 0.40 inch, to optimize pressure sensing without an air-blood interface using external sensors.

Also in a preferred embodiment, the passage 438 in the replacement fluid management module 426 that leads to the bypass tubing 432 (see FIG. 11) is formed with a channel width of between about 0.050 inch and 0.60 inch. The width is matched with pinch portion of regulator 242. This establishes the proper balanced flow conditions to prevent chamber overfilling. The foregoing dimensions and ranges are set forth solely for the purpose of illustrating typical device dimensions. The actual dimensions of a device constructed according to the principles of the present invention may obviously vary outside of the listed ranges without departing from those basic principles.

C. Representative Hemofiltration Modalities

During hemofiltration, blood is drawn from the person at a prescribed flow rate (BFR). Waste fluid is removed from the blood flow through filter 34 and volumetrically balanced with replacement fluid, which is returned in the venous blood flow at a prescribed rate (RFR). A prescribed net ultrafiltration volume of waste fluid is also removed at a prescribed flow rate (UFR) with fluid balancing, to control net weight loss. Operation of the machine 16 in a hemofiltration mode terminates when either (i) the replacement fluid sensor indicates the absence of replacement fluid flow by sensing the presence of air (i.e., no more replacement fluid) and the net ultrafiltration goal has been achieved; or (ii) the time prescribed for the session has elapsed.

Hemofiltration can also be performed without an ultrafiltration function (which can be called balanced hemofiltration). This mode can be used for persons that experience no weight gains between treatment sessions. This mode can also be used at the end of a hemofiltration session, when the net ultrafiltration goal was achieved before exhausting the supply of replacement fluid.

During another hemofiltration modality (called only net ultrafiltration), only a net ultrafiltration volume of waste is removed from the person. No fluid is replaced. This mode can be used when it is desired only to remove fluid. This mode can also be used at the end of a hemofiltration session, when the net ultrafiltration goal has not been achieved but the supply of replacement fluid has been exhausted.

In another hemofiltration modality (called replacement fluid bolus), there are no fluid balancing and ultrafiltration functions. Blood is circulated in an extracorporeal path and a bolus of replacement fluid is added. In the illustrated embodiment, the ultrafiltration pump 144 is run in reverse at a speed equal to the waste and replacement pump 152. This recirculates waste fluid through the waste compartments 212R and 214R, to add replacement fluid from the replacement compartments 212F and 214F to the patient. The waste fluid that is recirculated limits waste fluid removal through the hemofilter 34, yielding replacement fluid addition without additional waste fluid removal. The net volume of added replacement fluid conveyed to the patient equals the volume of waste fluid recirculated. This mode can be used to return fluid to a person in a bolus volume, e.g., during a hypotensive episode or during rinse back at the end of a given hemofiltration session.

1. Controlling the Blood Flow Rate

High blood flow rates (e.g., in some embodiments at least 200 ml/min or more, in other embodiments at least 300 ml/min or more, in other embodiments at least 400 ml/min or more, in other embodiments at least 500 ml/min or more, and in other embodiments at least 600 ml/min or more) are conducive to rapid, efficient frequent hemofiltration. The high blood flow rates not only reduce the processing time, but also significantly increases the transport rate of uremic toxins across the hemofiltration membrane. In this way, the system 10 removes high concentrations of uremic toxins, without requiring the removal of high fluid volumes, with the attendant loss of electrolytes.

The blood flow rate (BFR) can be prescribed by an attending physician and input by the operator at the beginning of a treatment session. Alternatively, the machine 16 can automatically control to achieve an optimal BFR and minimize procedure time, based upon a desired filtration fraction value (FF), ultrafiltration flow rate (UFR), and replacement fluid flow rate (RFR), as follows: BFR=(RFR+UFR)/FF where:

FF is the desired percentage of fluid to be removed from the blood stream through the hemofilter 34.

A desired FF (typically 20% to 35%) for post dilution HF can be either preset or prescribed by the attending physician. A desired FF takes into account the desired therapeutic objectives of toxin removal, as well as the performance characteristics of the hemofilter 34. A nominal FF can be determined based upon empirical and observed information drawn from a population of individuals undergoing hemofiltration. A maximum value of approximately 30% is believed to be appropriate for most individuals and hemofilters 34, to achieve a desired therapeutic result without clogging of the hemofilter 34.

In the illustrated embodiment, an arterial line sensor is incorporated into the extracorporeal circuit. The sensor 98 is an ultrasonic air leak detector, which also can provide the added capacity to sense flow rate.

In the illustrated embodiment, the machine 16 senses waste fluid pressure to control the blood flow rate to optimize the removal of fluid across the hemofilter 34. As arterial blood flows through the hemofilter 34 (controlled by the blood pump 92), a certain volume of waste fluid will cross the membrane into the waste line 118. The volume of waste fluid entering the waste line 118 depends upon the magnitude of the transmembrane pressure, or the pressure differential between the blood on the inside of filter fibers and the waste fluid on the outside of the fibers. As waste fluid is pumped away, the transmembrane pressure increases pushing waste fluid across membrane to replace removed waste. The transmembrane pressure is sensed by the sensor 132. The waste fluid pressure is adjusted by controlling the waste fluid removal rate through the fluid balancing compartments (i.e., through control of the waste and replacement pump 152) and through the UF pump 144.

The machine 16 monitors the waste fluid pressure at sensor 132. By keeping the pressure sensed by the sensor 132 slightly above zero (approximately 30 to 100 mmHg), the machine 16 achieves the maximum removal of fluid from the blood at the operative blood flow rate. Waste pressure values significantly higher than zero will limit removal of fluid from the blood and keep a higher percentage of waste fluid in the blood (i.e., result in a lower filtration fraction). However, this may be desirable for persons who tend to clot easier. The machine 16 can also include a waste pressure alarm to indicate when the sensed waste fluid pressure does not meet set criteria.

By sensing waste fluid pressure by sensor 132, the machine 16 also indirectly monitors arterial blood pressure and flow. At a constant blood pump speed, changes in arterial blood flow caused, e.g., by access clotting or increased arterial blood pressure, makes less waste fluid available in the waste line 118. At a given speed for pump 152, change in arterial blood flow will lower the sensed waste pressure at sensor 132 to a negative value, as fluid is now drawn across the membrane. The machine 16 adjusts for the change in arterial blood flow by correcting the waste fluid removal rate through the pump 152 and 144, to bring the waste pressure back to slightly above zero, or to another set value.

In this arrangement, a pressure sensor in the arterial blood line is not required. If the arterial pressure increases at a fixed blood pump speed, the blood flow must drop, which will result in a sensed related drop in the waste fluid pressure by the sensor 132. Adjusting the pump 152 and 144 to achieve a pressure slightly above zero corrects the reduced arterial blood flow. In this arrangement, since the waste fluid pressure is maintained at a slightly positive value, it is not possible to develop a reverse transmembrane pressure, which conveys waste fluid back to the person's blood. The maximum transmembrane pressure is the maximum venous pressure, since waste fluid pressure is held slightly positive.

In an alternative arrangement, arterial blood pressure can be measured by a sensor located upstream of the blood pump. The rate of the blood pump is set to maintain sensed arterial blood pressure at a predetermined control point. This controls the blood pump speed to a maximum rate. The control point can be determined, e.g., on a day-to-day basis, to take into account the blood access function of the person undergoing treatment. Use of an arterial pressure control point minimizes the treatment time, or, alternatively, if treatment time is fixed, the removal of waste fluid can maximized.

In this arrangement, safety alarms can be included should the sensed arterial pressure become more negative than the control point, along with a function to shut down the blood pump should an alarm occur.

In an alternative arrangement, a flow rate sensor can be placed in the arterial blood line to sense an actual blood flow rate. The sensed blood flow rate is compared to a commanded blood flow rate, and the blood pump is controlled to a commanded difference between the two flow rates. In this way, a maximum blood flow rate can be achieved. Alternatively, as arterial blood pressure can be expressed as a function of flow rate, arterial blood pressure can be derived from the sensed flow rate. The rate of the blood pump is set to maintain the derived arterial blood pressure at a predetermined control point. This controls the blood pump speed to a maximum rate. As stated above, use of an arterial pressure control point minimizes the treatment time, or, alternatively, if treatment time is fixed, the removal of waste fluid can be maximized by controlling waste fluid pressure, as described above.

2. Controlling the Replacement Fluid Flow Rate

RFR can be prescribed by an attending physician and inputted by the operator at the beginning of a treatment session.

Alternatively, the machine 16 can automatically control RFR to minimize procedure time based upon the desired filtration fraction value (FF), BFR, and UFR, as follows: RFR=(BFR*FF)−UFR.

In the illustrated embodiment, waste is conveyed to the waste side compartments 212R and 214R, and replacement fluid is conveyed to the replacement side compartments 212F and 214F, by operation of the dual header waste and replacement fluid pump 152. Alternatively, separate waste and replacement fluid pumps can be provided.

The speed of the waste and replacement pump 152 is controlled to achieve the desired RFR. The machine 16 cycles the inlet and outlet valve assemblies 244, 246, 248, and 250, as described. The machine 16 cycles between the valve states according to the speed of the waste and fluid pump 152 to avoid overfilling the compartments 212, 214 receiving fluid. Various synchronization techniques can be used.

In a preferred embodiment, the waste fluid is pumped at RFR, and the replacement fluid is pumped at a higher rate, but is subject to pressure relief through the pressure relief path 240 upon filling the corresponding replacement side compartment 212F and 214F.

In another arrangement, the timing of the transition between valve cycles is determined by active sensing of pressure within the compartments 212, 214 receiving liquid. As the two matching walls of chambers 212R/212F and 214R/214F reach the end of their travels, pressure will increase, signaling an end of cycle to switch valve states.

In yet another arrangement, the location of the two matching walls of chambers 212R/212F and 214R/214F as they reach the end of their travels are actively sensed by end of cycle sensors on the machine 16. The sensors can comprise, e.g., optical sensors, capacitance sensors, magnetic Hall effect sensors, or by radio frequency (e.g., microwave) sensors. The termination of movement of the walls indicates the complete filling of a compartment and the concomitant emptying of the other compartment, marking the end of a cycle. The sensors trigger an end of cycle signal to switch valve states.

The machine 16 counts the valve cycles. Since a known volume of replacement fluid is expelled from a replacement side compartment during each valve cycle, the machine 16 can derive the total replacement volume from the number of valve cycles. The replacement fluid volume is also known by the number of replacement fluid bags of known volume that are emptied during a given session.

Hemofiltration can be conducted without fluid replacement, i.e., only net ultrafiltration, by setting RFR to zero.

3. Controlling the Ultrafiltration Flow Rate

UFR can be prescribed by an attending physician and inputted by the operator at the beginning of a treatment session.

The speed of the ultrafiltration pump is monitored and varied to maintain UFR.

Frequent hemofiltration can be conducted without an ultrafiltration function, i.e., balanced hemofiltration, by setting UFR to zero.

4. Active Filtration Rate Control

In an alternative embodiment, the machine 16 also actively controls the filtration rate along with the blood flow rate, to achieve a desired magnitude of uremic toxin removal through the hemofilter 34.

In this embodiment, the machine 16 includes a flow restrictor which is positioned to engage a region of the venous blood return path 84 in the circuit 18. The restrictor comprises, e.g., a stepper-driven pressure clamp, which variably pinches a region of the venous blood return path upon command to alter the outlet flow rate of blood. This, in turn, increases or decreases the transmembrane pressure across the filter membrane.

For a given blood flow rate, waste transport across the filter membrane will increase with increasing transmembrane pressure, and vice versa. However, at some point, an increase in transmembrane pressure, aimed at maximizing waste transport across the filter membrane, will drive cellular blood components against the filter membrane. Contact with cellular blood components can also clog the filter membrane pores, which decreases waste transport through the membrane.

Filtration rate control can also rely upon an upstream sensor mounted on the machine 16. The sensor is positioned for association with a region of the arterial blood supply path between the blood pump 92 and the inlet of the hemofilter 34. The sensor senses the hematocrit of the blood prior to its passage through the filter membrane (which will be called the pre-treatment hematocrit). In the arrangement, a downstream sensor is also mounted on the machine 16. The sensor is positioned for association with a region of the venous blood return path downstream of the outlet of the hemofilter 34. The sensor senses the hematocrit of the blood after its passage through the hemofilter 34 (which will be called the post-treatment hematocrit).

The difference between pre-treatment and post-treatment hematocrit is a function of the degree of waste fluid removal by the hemofilter 34. That is, for a given blood flow rate, the more waste fluid that is removed by the hemofilter 34, the greater the difference will be between the pre-treatment and post-treatment hematocrits, and vice versa. The machine 16 can therefore derive an actual blood fluid reduction ratio based upon the difference detected by sensors between the pre-treatment and post-treatment hematocrits. The machine 16 periodically compares the derived fluid reduction value, based upon hematocrit sensing by the sensors, with the desired FF. The machine 16 issues a command to the flow restrictor to bring the difference to zero.

Waste fluid removal optimization can also be achieved by maintaining a maximum specified transmembrane pressure in the hemofilter by manipulating blood flow rate, and/or venous blood pressure, and/or waste fluid pressure. This optimization technique can be undertaken once at the outset of a given procedure, or at several intervals during the course of a procedure. In this arrangement, arterial blood pressure sensing (or derivation thereof based upon flow rate sensing) is implemented to achieve a maximum blood flow rate. A fixed or variable flow restrictor is placed in the venous blood return path to maintain a set maximum transmembrane pressure (e.g., 600 mmHg) while the maximum arterial blood flow rate is maintained. Pressure is sensed in the venous blood return path to assure that venous pressure does not exceed a set maximum amount (e.g., 250 mmHg), which is set for safety reasons. Waste fluid pressure is kept slightly above 50 mmHg. Together, control of transmembrane pressure at the maximum blood flow rate and control of waste fluid pressure at a maximum blood flow rate, maximize the waste fluid removal rate.

5. Set Up Pressure Testing/Priming

Upon mounting the disposable fluid circuit 18 on the machine 16, the pumps can be operated in forward and reverse modes and the valves operated accordingly to establish predetermined pressure conditions within the circuit. The sensors monitor build up of pressure within the circuit, as well as decrease in pressure over time. In this way, the machine can verify the function and integrity of pumps, the pressure sensors, the valves, and the flow paths overall.

The machine 16 can also verify the accuracy of the ultrafiltration pump using the fluid balancing containers.

Priming can be accomplished at the outset of each hemofiltration session to flush air and any residual fluid from the disposable fluid circuit. Fluid paths from the blood lines to the waste bag are flushed with replacement fluid. Replacement fluid is also circulated through the fluid balancing containers into the waste bag and the venous return path. The higher flow rate in the replacement fluid path and timing of the fluid balancing valve elements assure that the replacement fluid compartments completely fill and the waste fluid compartments completely empty during each cycle for priming.

6. Rinse Back

As previously described, waste fluid pressure is controlled and monitored to assure its value is always positive. Likewise, pressure between the blood pump and the hemofilter must also be positive, so that air does not enter this region of the circuit. Forward operation of the blood pump to convey arterial blood into the hemofilter establishes this positive pressure condition.

In this arrangement, no air sensing is required in the blood line, and a pressure sensor between the blood pump and the hemofilter is required.

7. Using the GUI

When configured to guide an operator to perform hemofiltration, or another treatment modality, the GUI 324 (see FIG. 19) can, e.g., include an array of icon-based touch button controls 326, 328, 330, and 332. For example, the controls can include an icon-based treatment start/select touch button 326, an icon-based treatment stop touch button 328, an icon-based audio alarm mute touch button 330, and an icon-based add fluid touch button 332.

An array of three numeric entry and display fields can appear between the icon-based touch buttons. The fields can comprise information display bars 334, 336, and 338, each with associated touch keys 340 to incrementally change the displayed information.

The associated touch keys 340 can be provided to point up (to increase the displayed value) or down (to decrease the displayed value), to intuitively indicate their function. The display bars 334, 336, and 338 and touch keys 340 can be shaded in different colors.

An array of status indicator bars can appear across the top of the screen. The left bar 342, when lighted, displays a safe color (e.g., green) to indicate a safe operation condition. The middle bar 344, when lighted, displays a cautionary color (e.g., yellow) to indicate a caution or warning condition and may, if desired, display a numeric or letter identifying the condition. The right bar 346, when lighted, displays an alarm color (e.g., red) to indicate a safety alarm condition and may, if desired, display a numeric or letter identifying the condition.

The display can also a processing status touch button 348. For example, the button 348, when touched, can change for a period of time (e.g., 5 seconds) the values displayed in the information display bars 334, 336, and 338, to show the corresponding current real time values, e.g., for a hemofiltration modality, the replacement fluid volumes exchanged (in the top display bar 334), the ultrafiltrate volume (in the middle display bar 336), and the blood volume processed (in the bottom display bar 338). The status button 348, when touched, can also show the elapsed procedure time in the left status indicator bar 342.

The display can also include a cartridge status icon 350. The icon 350, when lighted, can indicate that the cartridge 18 can be installed or removed from the machine 16.

In a preferred arrangement, the GUI 324 can employ a touch button input verification function, which monitors the information provided by the touch button controls. The input verification function inputs the information provided by a given touch button control both to the system control processor and to the system safety processor. The two processors communicate using an appropriate handshake protocol when the information received by the system control processor matches the information received by the system safety processor. The handshake allows information input to proceed for execution. The lack of a handshake between the system control processor and system safety processor indicates a possible information input error. In this instance, the GUI generates an error signal which requires a re-entry of the information input and a subsequent handshake before information input can proceed for execution.

As FIG. 19 shows, the interface can also include an infrared port 360 to support the telemetry function, as already described.

The GUI 324, though straightforward and simplified, enables the operator to set these various processing parameters for a given hemofiltration session in different ways.

For example, in one input mode for hemofiltration, the GUI 324 can prompt the operator by back-lighting the replacement fluid display bar 334, the ultrafiltration display bar 336, and the blood flow rate display bar 338. The operator follows the lights and enters the desired processing values using the associated touch up/down buttons 340. The GUI back-lights the start/select touch button 326, prompting the operator to begin the treatment. In this mode, the machine 16 controls the pumps to achieve the desired replacement fluid, ultrafiltration, and blood flow rates set by the operator. The machine terminates the procedure when all the replacement fluid is used and the net ultrafiltration goal is achieved.

In another input mode for hemofiltration, the operator can specify individual processing objectives, and the machine 16 will automatically set and maintain appropriate pump values to achieve these objectives. This mode can be activated, e.g., by pressing the start/select touch button 326 while powering on the machine 16. The GUI 324 changes the function of the display bars 334 and 336, so that the operator can select and change processing parameters. In the illustrated embodiment, the processing parameters are assigned identification numbers, which can be scrolled through and selected for display in the top bar 334 using the touch up/down keys 340. The current value for the selected parameter is displayed in the middle display bar 336, which the operator can change using the touch up/down keys 340.

In this way, the operator can, e.g., specify a desired filtration factor value (FF) along with a desired ultrafiltration flow rate (UFR) and replacement fluid flow rate (RFR). The machine will automatically control the blood pump rate (BFR), based upon the relationship BFR=(RFR+UFR)/FF, as already described.

Alternatively, the operator can specify a desired filtration factor value (FF) along with a desired ultrafiltration flow rate (UFR) and blood flow rate (BFR). The machine will automatically control the replacement fluid pump rate (RFR), based upon the relationship RFR=(BFR*FF)–UFR, as already described.

Alternatively, the operator can specify only an ultrafiltration volume. In this arrangement, the machine 16 senses waste fluid pressure to automatically control the blood flow rate to optimize the removal of fluid across the hemofilter 34, as previously described. Alternatively, the machine can automatically control the blood flow rate to optimize removal of fluid based a set control arterial blood pressure, as also already described. Still alternatively, the machine can automatically optimize the ultrafiltration flow rate and blood flow rate to achieve the desired net ultrafiltration volume.

In another mode, the operator can specify both replacement fluid volume and ultrafiltration volume to remove. In this arrangement, the machine performs a countdown of the sum of the two fluid volumes to minimize the duration of the treatment.

While particular devices and methods have been described, once this description is known, it will be apparent to those of ordinary skill in the art that other embodiments and alternative steps are also possible without departing from the spirit and scope of the invention. Moreover, it will be apparent that certain features of each embodiment can be used in combination with devices illustrated in other embodiments. Accordingly, the above description should be construed as illustrative, and not in a limiting sense, the scope of the invention being defined by the following claims.

I. System Overview

FIG. 1 shows a system 10 that is well suited for handling fluids in support of various types of blood processing and/or fluid exchange procedures. The system 10 includes a durable hardware component or machine 16 (see FIG. 2) and a removable fluid processing cartridge 18 (see FIG. 3) that is intended to be installed in operative association with the machine 16 for use (see FIGS. 4 to 6).

The system 10 is suitable for use in many diverse treatment modalities during which blood and/or fluid are conveyed to and from an animal body. In particular, the system 10 is well suited for treatment modalities during which one fluid is removed from the body and replaced with another fluid in a controlled fashion. Such modalities include, e.g., hemofiltration (HF), hemodialysis (HD), hemodialysis with hemofiltration (HDF), and peritoneal dialysis (PD).

For example, the system 10 can perform hemofiltration, e.g., to treat an individual whose renal function is impaired or lacking, according to different selected protocols. The system 10 can be adapted to perform hemofiltration at relatively high blood flow rates to enable relatively short session time intervals, as well as at lower blood flow rates and over longer session time intervals. The former protocol can be adopted to achieve hemofiltration three or more times a week. The latter protocol can be adapted to achieve an overnight treatment regime, which can be called "nightly hemofiltration." Nightly hemofiltration can be conducted at intervals less or more frequent than three times a week. Alternatively, the system 10 can be adapted to perform hemofiltration on an acute basis, or on an intermittent chronic basis, at virtually any prescribed time interval and treatment pattern that achieves the maintenance of uremic toxin levels within a comfortable range. Thus, the system 10 can be adapted to perform multiple hemofiltration treatments per day at varying session times, morning, afternoon, or night, or a combination thereof.

The system 10 can also just as readily be adapted to perform hemodialysis (HD) or hemodialysis with hemofiltration (HDF). The fluid balancing functions that the system 10 can perform, as will be described in greater detail later, can also be readily adapted for use, either individually or in combination, in systems intended to perform prescribed peritoneal dialysis modalities.

The type and make-up of fluids that the system 10 can balance can and will vary according to the particular treatment modality being performed, e.g., among waste fluid and replacement fluid (in HF or HDF); or replacement fluid and dialysis solution (in HD or HDF); or fresh peritoneal dialysis solution and spent peritoneal dialysis solution (in PD). The terminology employed in this Specification in characterizing a particular type or make-up of fluid, or as ascribing a source, destination, or direction of fluid flow in the context of describing one treatment modality is not intended to be interpreted as being limited to that particular type or make up of fluid or that particular flow source, destination, or direction. Rather, a person of skill in the art will readily appreciate that the fluid type and make up and the flow particulars relating to volumetric fluid balancing can vary with different treatment modalities.

A. Fluid Processing Machine

The machine 16 (see FIG. 2) is preferably lightweight and portable, presenting a compact footprint, suited for operation on a table top or other relatively small surface normally found, e.g., in a hospital room or in a home. The compact size of the machine 16 also makes it well suited for shipment to a remote service depot for maintenance and repair.

Desirably, the machine 16 includes an operator interface 44 (see FIG. 2). FIG. 19 shows a representative display 324 for the operator interface 44 for the machine. The display 324 comprises a graphical user interface (GUI), which, in the illustrated embodiment, is displayed by the interface 44 on the exterior of the door 28, as depicted in FIG. 2. The GUI can be realized, e.g., as a membrane switch panel, using an icon-based touch button membrane. The GUI can also be realized as a "C" language program.

The GUI 324 presents to the operator a simplified information input and output platform, with graphical icons, push buttons, and display bars. The icons, push buttons, and display bars are preferably back-lighted in a purposeful sequence to intuitively lead the operator through set up, execution, and completion of a given treatment session.

B. The Fluid Processing Cartridge

The processing cartridge 18 (see FIG. 3) provides the fluid interface for the machine 16. The fluid interface between the cartridge 18 and machine 16 makes possible a fast and convenient one step process for loading the cartridge 18 for use on the machine 16 (see FIGS. 4 to 6).

In one embodiment, the cartridge 18 establishes a fixed orientation for fluid circuit elements and their operative interface with the hardware elements, such as pumps, sensors, and clamps, on the machine 16. The fixed orientation requires that all safety and control elements on the cartridge 18 and machine 16 are brought into operative association in a single, straightforward loading step. Due to the cartridge 18, the operator cannot place one part of the fluid circuit into an operating condition with one or more hardware elements on the machine 16 without placing the entire fluid circuit into an operating condition with all the hardware elements, including safety systems, on the machine 16.

Desirably, the cartridge 18 makes possible the elimination of air-blood interfaces, and/or positive pressure monitoring. In association with the machine 16, the fluid cartridge 18 can also perform accurate, synchronized volumetric fluid balancing, without the need for weight sensing, as will be described in greater detail later.

The consolidation of all blood and fluid flow paths in a single, easily installed cartridge 18 avoids the potential of contamination, by minimizing the number of connections and disconnections needed during a given treatment session. By enabling a dwell or wait mode on the machine 16, the cartridge 18 can remain mounted to the machine 16 after one treatment session for an extended dwell or break period and allow reconnection and continued use by the same person in a subsequent session for any reason, for example, or in a continuation of a session following x-rays or testing.

The cartridge 18 can therefore provide multiple intermittent treatment sessions during a prescribed time period, without exchange of the cartridge 18 after each treatment session. The time of use confines are typically prescribed by the attending physician or technical staff for the treatment center to avoid bio-contamination and can range, e.g., from 48 hours to 120 hours, and more typically 72 to 80 hours. The cartridge 18 can carry a bacteriostatic agent that can be returned to the patient (e.g., an anticoagulant, saline, ringers lactate, or alcohol) and/or be refrigerated during storage.

The single step loading function can be accomplished in various ways. In the illustrated embodiment (see FIG. 2), the machine 16 includes a chassis panel 26 and a panel door 28. The door 28 moves on a pair of rails 31 in a path toward and away from the chassis panel 26 (as shown by arrows in FIG. 2). A slot 27 is formed between the chassis panel 26 and the door 28. As FIGS. 4 to 6 show, when the door 28 is positioned away from the panel 26, the operator can, in a simple vertical (i.e., downward) motion (see FIG. 4), move a fluid processing cartridge 18 into the slot 27 and, in a simple horizontal (i.e., sideway) motion (see FIG. 5), fit the cartridge 18 onto the chassis panel 26. When properly oriented, the fluid processing cartridge 18 may rest on the rails 31 to help position the cartridge 18. As FIG. 6 shows, movement of the door 28 toward the panel 26 engages and further supports the cartridge 18 for use on the panel 26. This position of the door 28 will be called the closed position.

The machine 16 preferably includes a latching mechanism 30 and a sensor 32 (see FIG. 2) to secure the door 28 and cartridge 18 against movement before enabling circulation of fluid through the cartridge 18.

The cartridge 18 can be constructed in various ways. FIG. 3 (in an assembled view) and FIG. 7 (in an exploded view) show an embodiment of a cartridge 18, which can be used to in association with the machine 16 to perform a selected treatment modality. In this embodiment, the cartridge 18 includes a preformed support frame 400 manufactured, e.g., by thermoforming polystyrene or another comparable material. The support frame 400 presents an exterior surface 402 (shown in plane view FIG. 8) and an oppositely facing interior surface 404 (shown in plane view in FIG. 9).

When installed for use on the machine 16, the exterior surface 402 is oriented toward the door 28, and the interior surface 404 is oriented toward the chassis panel 26. An icon 440 imprinted on the exterior surface 402 (see FIG. 8) guides the operator in mounting the frame 400 on the chassis panel 26 in the proper front-to-back and up-and-down orientation.

As FIG. 7 best shows, the interior surface 404 of the frame 400 carries a flexible fluid circuit 408. In the illustrated embodiment, the flexible fluid circuit 408 comprises one or more individual fluid management modules. The modules can be dedicated to different processing functions. For example, one module can handle fluid being removed from the body, while another module can handle fluid being supplied to the body. These processing functions can be synchronized by various means of orienting the modules with each other, and with the common hardware elements on the machine 16.

In the illustrated embodiment (see FIG. 7), two modules 424 and 426 are provided, which are shown individually in FIGS. 10 and 11, respectively. As FIG. 7 shows, lengths of flexible tubing 418 communicate with modules 424 and 426 of the flexible fluid circuit 408, to convey fluid to and from the modules 424 and 426. Together, the flexible fluid circuit 408 and tubing 418 form a fluid processing circuit 420.

The modules 424 and 426 themselves can be constructed in various ways, depending upon the particular processing functions that are intended to be performed.

In the illustrated embodiment (see FIGS. 10 and 11), the modules 424 and 426 take the form of fluid circuit bags 434 and 436. Each bag 434 and 436 is formed, e.g., by radio frequency welding together two sheets of medical plastic material (e.g., polyvinyl chloride). Each bag 434 and 436 includes an interior array of radio frequency seals forming fluid paths, chamber regions, sensor regions, and clamp regions.

In the illustrated embodiment, when secured to the interior surface 404 of the frame 400 (see FIGS. 7 and 9), the bag 434 rests over the bag 436, so that portions of the fluid circuits defined by the modules 424 and 426 overlay one another. As will be explained later, this makes possible synchronization of different processing functions using common hardware elements on the machine 16.

II. Telemetry for the System

The system 10 can also include a telemetry network 22 (see FIGS. 1 and 18). The telemetry network 22 provides the means to link the machine 16 in communication with other locations 254 via, e.g., cellular networks, digital networks, modem, Internet, or satellites. A given location 254 can, for example, receive data from the machine 16 at the treatment location or transmit data to a data transmission/receiving device 296 at the treatment location, or both. A main server 256 can monitor operation of the machine 16 or therapeutic parameters of the person undergoing the specified treatment. The main server 256 can also provide helpful information to the person undergoing the specified treatment. The telemetry network 22 can download processing or service commands to the data receiver/transmitter 296.

1. Remote Information Management

FIG. 18 shows a representative telemetry network 22 in association with a machine 16 that carries out a specified treatment modality. The telemetry network 22 includes the data receiver/transmitter 296 coupled to the machine 16. The data receiver/transmitter 296 can be electrically isolated from the machine 16, if desired. The telemetry network 22 also includes a main data base server 256 coupled to the data receiver/transmitter 296 and an array of satellite servers 260 linked to the main data base server 256.

The data generated by the machine 16 during operation is processed by the data receiver/transmitter 296. The data is stored, organized, and formatted for transmission to the main data base server 256. The data base server 256 further processes and dispenses the information to the satellite data base servers 260, following pre-programmed rules, defined by job function or use of the information. Data processing to suit the particular needs of the telemetry network 22 can be developed and modified without changing the machine 16.

The main data base server 256 can be located, e.g., at the company that creates or manages the system 10. The satellite data base servers 260 can be located, for example, at the residence of a designated remote care giver for the person, or at a full time remote centralized monitoring facility staffed by medically trained personnel, or at a remote service provider for the machine 16, or at a company that supplies the machine 16 or the processing cartridge 18.

Linked to the telemetry network 22, the machine 16 acts as a satellite. The machine 16 performs specified therapy tasks while monitoring basic safety functions and providing the person at the treatment location notice of safety alarm conditions for resolution. Otherwise, the machine 16 transmits procedure data to the telemetry network 22. The telemetry network 22 relieves the machine 16 from major data processing tasks and related complexity. It is the main data base server 256, remote from the machine 16, that controls the processing and distribution of the data among the telemetry network 22, including the flow of information and data to the person undergoing therapy. The person at the treatment location can access data from the machine 16 through the local data receiver/transmitter 296, which can comprise a laptop computer, handheld PC device, web tablet, cell phone, or any unit capable of data processing.

The machine 16 can transmit data to the receiver/transmitter 296 in various ways, e.g., electrically, by phone lines, optical cable connection, infrared light, or radio frequency, using cordless phone/modem, cellular phone/modem, or cellular satellite phone/modem. The telemetry network 22 may comprise a local, stand-alone network, or be part of the Internet.

For example, when the machine 16 notifies the person at the treatment location of a safety alarm condition, the safety alarm and its underlying data can also be sent to the main server 256 on the telemetry network 22 via the receiver/transmitter 296. When an alarm condition is received by the main server 256, the main server 256 can locate and download to the receiving device 296 the portion of the operator's manual for the machine that pertains to the alarm condition. Based upon this information, and exercising judgment, the operator/user can intervene with operation of the machine 16. In this way, the main server 256 can provide an automatic, context-sensitive help function to the treatment location. The telemetry network 22 obviates the need to provide on-board context-sensitive help programs for each machine 16. The telemetry network 22 centralizes this help function at a single location, i.e., a main server 256 coupled to all machines 16.

The telemetry network 22 can relay to an inventory server 262 supply and usage information of components used for the treatment modality. The server 262 can maintain treatment site-specific inventories of such items, such as cartridges 18, ancillary processing materials, etc. The company or companies that supply the machine 16, the processing cartridge 18, or the ancillary processing material to the treatment location 12 can all be readily linked through the telemetry network 22 to the inventory server 262. The inventory server 262 thereby centralizes inventory control and planning for the entire system 10, based upon information received in real time from each machine 16.

The telemetry network 22 can relay to a service server 264 hardware status information for each machine 16. The service server 264 can process the information according to preprogrammed rules, to generate diagnostic reports, service requests or maintenance schedules. The company or companies of the system 10 that supply or service the machine 16 can all be readily linked through the telemetry network 22 to the service server 264. The service server 264 thereby centralizes service, diagnostic, and maintenance functions for the entire system 10. Service-related information can also be sent to the treatment location 12 via the receiving device 296.

The telemetry network 22 can also relay to a treatment monitoring server 266, treatment-specific information pertaining to the therapy provided by each machine 16. Remote monitoring facilities 268, staffed by medically trained personnel, can be readily linked through the telemetry network 22 to the treatment monitoring server 266, which centralizes treatment monitoring functions for all treatment locations served by the system 10.

The telemetry network 22 can also provide through the device 296 an access portal for the person undergoing treatment to the myriad services and information contained on the Internet, e.g., over the web radio and TV, video, telephone, games, financial management, tax services, grocery ordering, prescriptions purchases, etc. The main server 256 can compile diagnostic, therapeutic, and/or medical information to create a profile for each person served by the system 10 to develop customized content for that person. The main server 256 thus provide customized ancillary services such as on line training, billing, coaching, mentoring, uplinks to doctors, links to patient communities, and otherwise provide a virtual community whereby persons using the system 10 can contact and communicate via the telemetry network 22.

The telemetry network 22 thus provides the unique ability to remotely monitor equipment status, via the internet, then provide information to the user, also via the internet, at the location of the equipment. This information can include, e.g., what page of the operator's manual would be the most helpful for their current operational situation, actual data about the equipment's performance (e.g., could it use service, or is it set up based on the caretaker's recommendations), data about the current session, i.e., buttons pressed, alarms, internal machine parameters, commands, measurements.

The remote site can monitor the equipment for the same reasons that the user might. It can also retrieve information about the machine 16 when it is turned off because the telemetry device is self-powered. It retains all information about the machine over a period of time (much like a flight recorder for an airplane).

2. On-Site Programming

The main server 256 on the telemetry network 22 can also store and download to each machine 16 (via the device 296) the system control logic and programs necessary to perform a desired treatment modality. Programming to alter a treatment protocol to suit the particular needs of a single person at a treatments site can be developed and modified without a service call to change the machine 16 at any treatment location, as is the current practice. System wide modifications and revisions to control logic and programs that condition a machine 16 to perform a given treatment protocol can be developed and implemented without the need to retrofit each machine 16 at all treatment locations by a service call. This approach separates the imparting of control functions that are tailored to particular procedures, which can be downloaded to the machine 16 at time of use, from imparting safety functions that are generic to all procedures, which can be integrated in the machine 16.

Alternatively, the control logic and programs necessary to perform a desired treatment protocol procedure can be carried in a machine readable format on the cartridge 18. Scanners on the machine 16 automatically transfer the control logic and programs to the machine 16 in the act of loading the cartridge 18 on the machine 16. Bar code can be used for this purpose. Touch contact or radio frequency silicon memory devices can also be used. The machine 16 can also include local memory, e.g., flash memory, to download and retain the code.

For example, as FIG. 2 shows, the machine 16 can include one or more code readers 270 on the chassis panel 26. The frame 400 carries, e.g., on a label or labels, a machine readable (e.g., digital) code 272 (see FIG. 3) that contains the control logic and programs necessary to perform a desired treatment protocol using the cartridge 18. Loading the cartridge 18 on the machine 16 orients the code 272 to be scanned by the reader(s) 270. Scanning the code 272 downloads the control logic and programs to memory. The machine 16 is thereby programmed on site.

The code 272 can also include the control logic and programs necessary to monitor use of the cartridge 18. For example, the code 272 can provide unique identification for each cartridge 18. The machine 16 registers the unique identification at the time it scans the code 272. The machine 16 transmits this cartridge 18 identification information to the main server 256 of the telemetry network 22. The telemetry network 22 is able to uniquely track cartridge 18 use by the identification code throughout the system 10.

Furthermore, the main server 256 can include preprogrammed rules that prohibit multiple use of a cartridge 18, or that limit extended uses to a prescribed period of time. An attempted extended use of the same cartridge 18 on any machine 16, or an attempted use beyond the prescribed time period, will be detected by the machine 16 or the main server 256. In this arrangement, the machine 16 is disabled until an unused cartridge 18 is loaded on the machine 16.

Prior to undertaking set up pressure testing and priming of the cartridge 18, the machine 16 can also be conditioned to sense, e.g., by ultrasonic means, the presence of fluid in the cartridge. The presence of fluid indicates a reprocessed cartridge. In this arrangement, the machine 16 is disabled until a dry, unused cartridge 18 is loaded on the machine 16.

Service cartridges can also be provided for the machine 16. A service cartridge carries a code that, when scanned by the reader or readers on the chassis panel 26 and downloaded to memory, programs the machine 16 to conduct a prescribed service and diagnostic protocol using the service cartridge 18.

III. Representative Systems for Conducting Hemofiltration

The particular configuration of the machine 16 and the fluid processing circuit 420, which the tubing 418 and flexible fluid circuit 408 form, can vary according to the processing objectives of the system 10. As before stated, the system 10 is well suited for treatment modalities during which one fluid is removed from the body and replaced with another fluid in a controlled fashion, e.g., hemofiltration (HF), hemodialysis (HD), hemodialysis with hemofiltration (HDF), and peritoneal dialysis (PD).

For the purpose of illustration, FIG. 12 schematically shows a fluid circuit FC(HF) for carrying out hemofiltration. The fluid circuit FC(HF) supports the removal of blood from an individual and the separation of waste fluid from the blood using a hemofilter 34. The fluid circuit FC(HF) also supports the return of treated blood and replacement fluid to the individual. The fluid circuit FC(HF) also supports an ultrafiltration function.

The flexible fluid circuit 420 carried by the frame 400 and the machine 16 can be readily configured to form this circuit FC(HF) and thereby conduct hemofiltration. A person of skill in the art will readily appreciate how the fluid circuit 420 and machine 16 can be configured to perform other treatment modalities, as well.

In the illustrated implementation, the first module 424 is configured to handle waste fluid, and the second module 426 is configured to handle replacement fluid.

As FIG. 10 shows, the waste fluid management module 424 includes fluid waste balancing chambers 212R/214R and associated waste fluid clamp regions 220 and 222. The location of these elements in the fluid circuit FC(HF) are also shown schematically in FIG. 12.

As FIG. 11 shows, the replacement fluid management module 426 includes corresponding replacement fluid balancing chambers 212F/214F and associated replacement fluid clamp regions 224 and 226. The location of these elements in the fluid circuit FC(HF) are also shown schematically in FIG. 12.

When the modules 424 and 426 are mounted against the interior surface 404 of the frame 400 (see FIG. 9), the chambers 212R/214R and 212F/214F and the clamp regions 222/220 and 224/226 communicate in the same plane. When the frame 400 is mounted for use on the machine 16, the overlaying chambers 212R/214R and 212F/214F and clamp regions 222/220 and 224/226 operatively engage common machine elements on the machine 16 to carry out volumetric fluid balancing of replacement fluid in proportion to waste removal, without use of weight sensors. When the frame 400 is mounted for use on the machine 16, the modules 424 and 426, in association with hardware elements on the machine 16, also accomplish ultrafiltration.

In the illustrated embodiment (see FIGS. 7 and 8), an exterior surface 406 of the frame 400 is slightly recessed or concave. When the frame 400 is mounted on the machine 16, this recessed frame surface 406 nests within a correspondingly raised surface 407 on the door 28 (see FIG. 13). When so nested, convex or domed frame regions 412, which project above the surface 406 of the frame 400 (see FIGS. 7 and 8) fit within mating concave indentations 206' and 208' on the door 28.

The fluid balancing chambers 212R/214R and 212F/214F rest in an overlying relationship within these domed regions 412 on the opposite interior surface 404 of the frame 400 (see FIG. 8). When the frame 400 is mounted on the machine 16, and the door 28 closed, the interior surface 404 faces the chassis panel 28, and the fluid balancing chambers 212R/214R and 212F/214F rest within concave indentations 206 and 208 formed on the chassis panel 26 (see FIG. 2). When the frame 400 is mounted on the machine 16, and the door 28 closed, the flexible chambers 212R/214R and 212F/214F are thereby enclosed between the indentations 206/208 on the chassis panel 26 and the convex regions 412 of the frame 400 (which themselves nest within the concave indentations 206'/208' on the door 28). Expansion of the flexible chambers 212R/214R and 212F/214F as a result of fluid introduction is thereby restrained to a known maximum volume, generally approximately between 10 and 50 cc, preferably approximately between 20 and 40 cc, more preferably approximately 25 cc, defined between the chassis chambers 206/208 and the convex frame regions 412.

As FIG. 8 shows, cut-outs 410 in the surface 406 expose the overlaying flexible clamp regions 222/220 and 224/226 to contact with the four clamping pads 450 mounted on the door 28 (see FIG. 13) and hardware clamping elements 244, 246, 248, and 250 on the chassis panel 26 (see FIG. 2). In operation, the clamping elements 244, 246, 248, and 250 are caused to project from the chassis panel 26 to press the overlying clamp regions 222/220 and 224/226 against the clamping pads 450 on the door 28. Synchronized valve functions are thereby made possible, as will be described later.

Referring back to FIG. 8, another cut-out 413 in the surface 406 exposes a portion of the fluid circuit 408 for blood leak sensing functions, as will also be described later.

Surrounding the surface 406 are recessed channel regions 414a to 414j, which are formed in the exterior surface 402. These recessed channel regions 414a to 414j (identified in FIG. 8) accommodate the passage of the lengths of flexible tubing 418 that communicate with the flexible fluid circuit 408, to form the fluid processing circuit 420. The recessed regions 414a to 414j form channels that guide and restrain the tubing 418 within the frame 400. Multiple cut-outs 442a to 442i are formed along the recessed regions 414a to 414j, to expose intervals of the tubing 418 for engagement with clamps or sensors on the machine 16, as will be described.

As FIG. 7 show, a cover member 416 made, e.g., from rigid or semi-rigid paper or plastic, is desirably secured to the exterior surface 402 of the frame 400 to overlay and close the recessed channel regions 414, in which the tubing 418 is carried (FIG. 3 shows the exterior surface 402 with the cover member 416 installed).

As FIG. 8 shows, portions of tubing 418 extend beyond the support frame 400 for connection with the patient and other external items making up the fluid processing circuit 420, as will be described later. Cartridge 18 may extend beyond the edge of machine 16.

Portions of the tubing 418 also communicate with peristaltic pump tubes 94, 145, 155, and 201 located in the surface 406 (see FIG. 8). Cut-outs 446a to 446c are formed in the region 406 beneath the pump tubes 94, 145, 144, and 201, to expose the pump tubes 94, 145, 144, and 201 for engagement with the corresponding peristaltic pump rollers 92, 144, and 152 on the chassis panel 26 (see FIG. 2) and the corresponding pump races 362 on the door 28 (see FIG. 13).

Further regarding the configuration of the fluid processing circuit 420 (see FIG. 8), as adapted to conform to the hemofiltration circuit FC(HF) shown in FIG. 12, the flexible tubing 72 forms the arterial blood supply path, with an appropriate distal connector to couple to an arterial blood access site. The tubing 72 is guided by a recessed channel 414a into the frame 400. Cut-outs 442a and 442b expose the tubing 72 for engagement with an arterial blood line air sensor 98 and arterial blood line clamp 96.

The tubing 72 is coupled with the pump tube 94, which spans the cut-out 446a in the frame 400, for engagement with the blood pump 92 on the chassis panel 26 (see FIG. 2).

Tubing 78 extends from the pump tube region 94 in a recessed channel 414b in the frame 400. The tubing 78 extends beyond the frame 400 and includes the connector 82 to couple the arterial blood path to the inlet of a hemofilter 34 (see FIG. 12).

The placement of the cut-out 442a (and associated air sensor 98 on the machine 16) upstream of the hemofilter 34 allows air bubbles to be detected prior to entering the hemofilter 34. This location is desirable, because, in the hemofilter 34, air bubbles break up into tiny micro-bubbles, which are not as easily detected as bubbles upstream of the hemofilter 34. Placement of the air sensor 98 upstream of the hemofilter 34 also serves the additional purpose of detecting air when the blood pump 92 is operated in reverse, to rinse back blood to the patient. The air sensor 98 also detects if the arterial blood line is clamped or otherwise occluded, to thereby allow terminate operation of the arterial blood pump 92 when this condition occurs. Air sensor 98 can also sense a clamped or occluded arterial line while the pump turns. The resulting negative pressure degasses the blood which is sensed by the air sensor, and an alarm is sounded. If air by chance enters the arterial blood line, e.g., by a faulty connection or an air leak, the air sensor 98 will detect this condition and terminate operation of the arterial blood pump before the air enters the hemofilter.

As FIG. 8 shows, the tubing 84 extends beyond the frame 400 and includes a distal connector 86 to couple to the blood outlet of the hemofilter 34 (see FIG. 12). The tubing 84 is led across the frame 400 through a recessed channel 414c. Cutaway regions 442c and 442d on the frame 400 expose the tubing 84 for engagement with the venous blood line air sensor 108 and venous S blood line clamp 112 (see FIG. 12). The tubing 84 then extends beyond the frame 400, and carries an appropriate distal connector to couple to venous blood access site.

As FIG. 8 shows, the flexible tubing 118 extends beyond the frame 400 and carries a distal connector 120 to couple to the waste outlet of the hemofilter 34 (see FIG. 12). The tubing 118 thereby serves to convey waste fluid for fluid balancing and discharge. The flexible tubing 118 enters a recessed channel 414d in the frame 400 and joins a connector C8. The connector C8 couples the tubing 118 to the waste fluid management module 424, and through the module 424 to ultrafiltration pump tube 145 (through connector C1) and the waste pump tube 155 (through connector C7). The pump tube 145 spans a cut-out 446c in the frame 400 to connector C2, for engagement with the ultrafiltration pump 144 on the chassis panel 26 (see FIG. 2). The pump tube 155 spans a cut away region 446d in the frame 400 to connector C3, for engagement with the waste fluid header region 154 of the dual header waste and replacement pump 152 on the chassis panel 26 (see FIG. 2).

Connectors C2 and C3 are fluidically coupled via the waste fluid management module 424 (see FIG. 10) to connectors C10 and C4. As FIG. 8 shows, the flexible tubing 122 is coupled by the connector C4 to an outlet of the waste management module 424. The tubing 122 is guided through a recessed channel 414e in the support frame 400. Cut-away region 442e on the frame 400 expose the tubing 122 for engagement with the waste line clamp 166. The tubing 122 then extends beyond the frame 400, with an appropriate distal connector 124 to couple to a waste bag or an external drain. It is through this tubing 122 that waste fluid is discharged after fluid balancing. An in-line air break 170 (see FIG. 12) can be provided in communication with the tubing 122 downstream of the waste clamp 166, to prevent back flow of contaminants from the waste bag or drain.

Referring to FIG. 8, the flexible tubing 172 serves to convey replacement fluid. The tubing 172 extends outside the frame 400 and includes a distal connector 174 that enables connection to multiple containers of replacement fluid 176 (see FIG. 12). The tubing 172 is guided by a recessed channel 414f within the frame 400. Cut-away regions 442f and 442g on the frame 400 expose the tubing 172 for engagement with an in line air sensor 182 and replacement fluid clamp 188 (see FIG. 12).

Flexible tubing 430 is guided through a recessed channel 414g in the support frame 400 between two t-connectors, one in the arterial blood tubing 72 and the other in the replacement tubing 172. The tubing 430 serves as the priming or bolus branch path 192, as will be described. A cut-away region 442h on the frame 400 exposes the tubing 430 for engagement with the priming clamp 194 on the machine 16 (see FIG. 12).

The replacement fluid tubing 172 is further guided by the recessed channel 414h in the frame 400 to the replacement fluid pump tube 201 (previously described), which is also coupled via a connector C5 to the replacement fluid management module 426 of the flexible fluid circuit 408. As FIG. 11 also shows, connector C5 is also fluidically coupled via the replacement fluid management module 426 to the connectors C6 and C9. The pump tube 201 spans the cut away region 446d in the frame 400, for engagement with the replacement fluid header region 200 of the dual header waste and replacement pump 152 on the chassis panel 26 (see FIG. 2).

Flexible tubing 432 is coupled by a connector C6 to the replacement fluid module 426. The flexible tubing 432 is guided through a recessed channel 414i in the support frame to a t-connector, which joins the replacement tubing 172 in the region immediately downstream of the connection with the replacement fluid pump tube 201. The tubing 432 serves as the relief path 240 that prevents overfilling of the fluid balancing compartments, as will be described.

Flexible tubing 428 is coupled by a connector C9 to the replacement fluid management module 426. The tubing 428 is guided through a recessed channel 414j in the support frame 400 in a small loop outside the frame 400 and is coupled by a t-connector to the venous blood return tubing 84. It is through this path that replacement fluid is added to the venous blood being returned to the patient.

The bags 434 and 436 are secured in overlaying alignment to the interior surface 404 of the frame 400 by the connectors C1 to C10, previously described.

FIG. 10 shows the waste management fluid circuit contained in the bag 434, as it would appear if viewed from interior surface 404 of the support frame 400 (as FIG. 9 also shows). The bag 434 is shown in association with the ultrafiltration pump tube 145 and waste fluid pump tube 155 that are also carried on the region 406 of the support frame 400.

The fluid circuit in the bag 434 includes the waste path 138 that leads to the waste side compartments 212R and 214R (for fluid balancing) by way of the waste pump 155 and the waste path 136 by way of the ultrafiltration pump 145 that bypasses the waste side compartments 212R and 214R (for ultrafiltration). The flow paths in the waste fluid circuit in the bag 434 also include the exposed waste inlet clamp regions 220, to engage the valve assemblies 246 and 248 to control inflow of waste fluid into the waste compartments 212R and 214R, and the exposed waste outlet clamp regions 222, to engage the valve assemblies 244 and 250 to control outflow of waste fluid from the waste compartments 212R and 214R. The fluid circuit also includes the pressure sensor region 160, to engage the pressure sensor 156 (see FIG. 15) downstream of the waste and replacement fluid pump 152.

FIG. 11 shows the replacement fluid management circuit contained in the bag 436, as it would appear if viewed from the interior surface 404 of the support frame 400 (as FIG. 8 also shows). The bag 436 is shown in association with the replacement fluid pump tube 201 that is also carried in the region 406 of the support frame 400. The replacement fluid pump tube 201 is located alongside the waste fluid pump tube 155, on region 200 for concurrent engagement with the dual header waste and replacement pump 152 on the chassis panel 26 (see FIG. 2).

The fluid circuit in the bag 436 includes the replacement fluid paths which lead to and from the replacement side compartments 212F and 214F. The fluid circuit also includes the inlet clamp regions 224, to engage the valve assemblies 244 and 250 on the machine 16 to control inflow of replacement fluid into the replacement side compartments 212F and 214F; and the outlet clamp regions 226, to engage the valve assemblies 246 and 248 on the machine 16 to control outflow of replacement fluid from the replacement side compartments 212F and 214F. The fluid circuit includes a sensor region 204, to engage the pressure sensor 202 (see FIG. 15) downstream of the waste and replacement pump 152.

When the bags 434 and 436 are mounted in overlaying relationship on the interior frame surface 404 (as FIG. 9 shows), the replacement side compartments 212F and 214F and the waste side compartments 212R and 214R together rest in the convex recesses 412 in the region 406 of the exterior frame surface 402. The inlet clamp regions of the waste compartments 212R and 214R formed on the waste panel 234 overlay the outlet clamp regions of the replacement compartments 212F and 214F formed on the replacement panel 232, and vice versa.

The entry and exit paths serving the waste and replacement compartments formed in the bags 434 and 436 (shown in FIG. 9) are all located at the top of the chambers 212R, 214R, 212F, and 214F. Priming is achieved, as the paths are top-oriented. Furthermore, due to the overlaying relationship of bags 434 and 436, the clamping regions 220, 222, 224, and 226 are arranged to overlay one another. The overlaying arrangement of the clamping regions 220, 222, 224, and 226 serving the waste and replacement compartments simplifies the number and operation of the inlet and outlet valve assemblies 216 and 218 on the machine 16. Since the inlet clamp regions 224 for the replacement compartments 212F and 214F overlay the outlet clamp regions 222 for the waste compartments 212R and 214R, and vice versa, only four clamping elements 244, 246, 248, 250 need be employed to simultaneously open and close the overlaying eight clamp regions.

1. Achieving Synchronized Volumetric Fluid Balancing

In use, as FIG. 14 shows, the first clamping element 244 is movable into simultaneous clamping engagement with the inlet clamp region 224 of the replacement compartment 212F (in the replacement fluid module bag 436) and the outlet clamp region 222 of the waste compartment 212R (in the waste fluid module bag 434), closing both. Likewise, the fourth clamping element 250 is movable into simultaneous clamping engagement with the inlet clamp region 224 of the replacement compartment 214F (in the replacement fluid module bag 436) and the outlet clamp region 222 of the waste compartment 214R (in the waste fluid module bag 434).

The second clamping element 246 is movable into simultaneous clamping engagement with the outlet clamp region 226 of the replacement compartment 212F and the inlet clamp region 220 of the waste compartment 212R, closing both. Likewise, the third clamping element 248 is movable into simultaneous clamping engagement with the outlet clamp region 226 of the replacement compartment 214F and the inlet clamp region 220 of the waste compartment 214R, closing both.

The machine 16 toggles operation of the first and third clamping elements 244, 248 in tandem, while toggling operation the second and fourth clamping elements 246, 250 in tandem. When the first and third clamping elements 244, 248 are operated to close their respective clamp regions, replacement fluid enters the replacement compartment 214F to displace waste fluid from the underlying waste compartment 214R, while waste fluid enters the waste compartment 212R to displace replacement fluid from the overlaying replacement compartment 212F. When the second and fourth clamping elements 246, 250 are operated to close their respective clamp regions, replacement fluid enters the replacement compartment 212F to displace waste fluid from the underlying waste compartment 212R, while waste fluid enters the waste compartment 214R to displace replacement fluid from the overlaying replacement compartment 214F.

FIGS. 15 and 16 show a mechanically linked pump and valve system 300 that can be arranged on the chassis panel 26 of the machine 16 and used in association with the flexible fluid circuit 408.

The system 300 includes three electric motors 302, 304, and 306. The first motor 302 is mechanically linked by a drive belt 308 to a dual header waste and replacement pump 152. The second motor 304 is mechanically linked by a drive belt 310 to a blood pump 92. The third motor 306 is mechanically linked by a drive belt 312 to an ultrafiltration pump 144.

A drive belt 314 also mechanically links the first motor to the first, second, third, and fourth clamping elements 244, 246, 248, and 250, via a cam actuator mechanism 316. The cam actuator mechanism 316 includes, for each clamping element 244, 246, 248, and 250 a pinch valve 318 mechanically coupled to a cam 320. The cams 320 rotate about a drive shaft 322, which is coupled to the drive belt 314.

Rotation of the cams 320 advances or withdraws the pinch valves 318, according to the surface contour machined on the periphery of the cam 320. When advanced, the pinch valve 318 closes the overlying clamp regions of the fluid circuit module bags 424 and 426 that lay in its path. When withdrawn, the pinch valve 318 opens the overlying clamp regions.

The cams 320 are arranged along the drive shaft 322 to achieve a predetermined sequence of pinch valve operation. During the sequence, the rotating cams 320 first simultaneously close all the clamping elements 244, 246, 248, and 250 for a predetermined short time period, and then open clamping elements 244 and 248, while closing clamping elements 246 and 250 for a predetermined time period. The rotating cams 320 then return all the clamping elements 244, 246, 248, and 250 to a simultaneously closed condition for a short predetermined time period, and then open clamping elements 246 and 250, while closing clamping elements 244 and 248 for a predetermined time period.

The sequence is repeated and achieves the balanced cycling of replacement fluid and waste fluid through the module bags 424 and 426, as previously described. A chamber cycle occurs in the time interval that the valve elements 244, 246, 248, and 250 change from a simultaneously closed condition and return to the simultaneously closed condition.

In a preferred embodiment (see FIG. 17), each clamping element 244, 246, 248, and 250 comprises a valve pin 500 movable within a valve slot 506 in the chassis panel 26. A rotating bearing surface 502 at one end of the valve pin 500 rides on the cam surface 504 of the corresponding rotating cam 320. As the cam 320 rotates, the cam surface 504 presents regions of increasing or decreasing radius, causing the pin 500 to reciprocate within the valve slot 506 toward and away from the door 28, which, during use of the fluid circuit 408, faces the chassis panel 26 in the closed position.

A pinch valve 318 is carried at the opposite end of the valve pin 500. The pinch valve 318 includes a pinch valve chamber 508, in which the valve pin 500 rests. A spring 510 in the pinch valve chamber 508 couples the pinch valve 318 to the valve pin 500. The spring 510 applies a fixed valve force against the pinch valve 318, in the absence of physical contact between the end of the valve pin 500 and the pinch valve 318. The spring 510 thereby mediates against over- and under-valving effects as a result of small changes in tolerance between the pin 500 and pinch valve 318, fluid circuit module bag 424 and 426 thickness, and the closed gap between door 28 and chassis 26.

When mounted for use on the chassis panel 26, with the door 28 closed, the fluid circuit 408 is sandwiched between the panel 26 and the door 28. Each pinch valve 318 is aligned with a valve plate 512 carried by the door 28. The valve plate 512 is made from a hard plastic or metallic material. The valve plate 512 rests against a disk 514 on the door 28, which can be made of rubber or another elastomeric material. The disk 514, which can also be a spring, allows the valve plate 512 to move or "float" when the pinch valve applies a valve force. The valve plate 512 thereby accounts for any lack of perpendicularity between the pinch valve 318 and the valve plate 512.

Movement of the pinch valve 318 toward the door 28 (as the cam surface 504 presents regions of increasing radius) pinches the intermediate, aligned clamp region in the fluid circuit 56 (comprised of modules 424 and 426 overlying one another) between the pinch valve 318 and the valve plate 512, thereby closing the valve region. Likewise, movement of the pinch valve 318 toward the door 28 (as the cam surface 504 presents regions of decreasing radius) separates the pinch valve 318 from the valve plate 514, thereby opening the intermediate valve region. The cam actuator mechanism 316 mechanically links the clamping elements 244, 246, 248, and 250 ratiometrically with the first motor 302. As the motor 302 increases or decreases the speed of the dual header waste and replacement pump 152, the operation of the clamping elements 244, 246, 248 and 250 increases or decreases a proportional amount.

In a preferred embodiment, the ratio is set so that the flow rate per unit time through the waste pump header region 154 (i.e., through waste path 434) approximately equals three-fourths of the volume of the waste compartment 212R/214R, while maintaining the cycle rate of 10 cycles per minute for a waste fluid flow rate of approximately 200 ml/min. For example, if the chamber volume is 25 cc, the cycle occurs after 18 to 21 cc of waste fluid enters the compartment. In other embodiments, the cycle rate is 9-11 cycles per minute for a waste fluid flow rate of approximately 180-220 ml/min, or the cycle rate is 8-12 cycles per minute for a waste fluid flow rate of approximately 160-240 ml/min.

In the illustrated embodiment, the waste pump header 155 is made smaller in diameter than the replacement fluid header 201. Thus, during operation of the dual header pump 152, which is made up of pump regions 154 and 200, the flow rate through the replacement fluid header region 200/201 (through replacement fluid path 426) will always be larger than the flow rate through the waste pump header region 154/155 (through waste path 424). Due to the higher flow rate through the replacement fluid path 426, a pressure relief path 438 (see FIG. 1) and 432 (see FIGS. 12 and 8) with pressure relief bypass valve 242 (see FIG. 15) is provided, to prevent overfilling. In the illustrated embodiment, the valve 242 is a mechanically spring biased pressure regulator, and serves the pressure regulation and bypass function of the machine 16.

In this arrangement, the in-line compartment that receives waste fluid will fill to approximately three-fourths of its volume during each cycle, displacing an equal amount of replacement fluid from its companion compartment. At the same time, the other in-line compartment that receives replacement fluid will fill completely. If the compartment completely fills with replacement fluid before the end of the cycle, the pressure relief bypass valve 242 (see FIG. 15) will open to circulate replacement fluid through the relief path 240, made up of 438, C6, and 432 (see FIG. 12), to prevent overfilling. During the next cycle, waste fluid in the compartment will be completely displaced by the complete fill of replacement fluid in its companion compartment.

The provision of a higher flow rate in the replacement fluid path also facilitates initial priming (as will be described later) only several chamber cycles are required to completely prime the in-line containers 212 and 214 with replacement fluid before fluid balancing operations begin.

The pump and valve system 300 used in association with the fluid circuit 408 achieves accurate fluid balancing, e.g., during hemofiltration, hemodialysis, hemodialysis with hemofiltration, and peritoneal dialysis.

B. Fluid Flow Path Dimensions

In one embodiment, key functional regions within the flexible fluid circuits are formed to possess dimensions that lay within critical ranges, to thereby achieve desired fluid flow conditions, pressure sensing conditions, fluid balancing functions, and valve functions. For example, each fluid balancing chamber 212 F/R and 214 F/R is formed to have a height (measured between the bottom of the chamber and the clamp regions) of between about 3.25 inches and about 5.0 inches, with a nominal height of about 3.6 inches. In this embodiment, each fluid balancing chamber 212 F/R and 214 F/R is formed to have a width (measured between the sides of the chamber and determined by the width of pinch clamp 318) of between about 1.0 inch and about 2.75 inches, with a nominal width of about 1.2 inches. These dimensions help optimize volumetric fluid balance functions.

Further, in another embodiment, each clamp region 220/222 and 224/226 is formed to have a channel width of between about 0.10 inch and 0.40 inch. Bead suppression measures are employed in the clamp regions 220/222 and 224/226 to keep the material adjacent the welded seams, which form the clamp regions, from exceeding more than twice the thickness of the material walls. These steps assure reliable functioning of the overlaying clamp regions in association with the external clamps.

Also, in another embodiment, the ultrafiltration fluid path 136 is formed to have a channel width of greater than about 0.140 inch but less than about 0.60 inch. This optimizes the flow of waste fluid.

In a preferred embodiment, the regions where pressure is sensed in the fluid circuit is formed to have in an interior diameter that is greater than 0.40 inch, to optimize pressure sensing without an air-blood interface using external sensors.

Also in a preferred embodiment, the passage 438 in the replacement fluid management module 426 that leads to the bypass tubing 432 (see FIG. 11) is formed with a channel width of between about 0.050 inch and 0.60 inch. The width is matched with pinch portion of regulator 242. This establishes the proper balanced flow conditions to prevent chamber overfilling. The foregoing dimensions and ranges are set forth solely for the purpose of illustrating typical device dimensions. The actual dimensions of a device constructed according to the principles of the present invention may obviously vary outside of the listed ranges without departing from those basic principles.

C. Representative Hemofiltration Modalities

During hemofiltration, blood is drawn from the person at a prescribed flow rate (BFR). Waste fluid is removed from the blood flow through filter 34 and volumetrically balanced with replacement fluid, which is returned in the venous blood flow at a prescribed rate (RFR). A prescribed net ultrafiltration volume of waste fluid is also removed at a prescribed flow rate (UFR) with fluid balancing, to control net weight loss. Operation of the machine 16 in a hemofiltration mode terminates when either (i) the replacement fluid sensor indicates the absence of replacement fluid flow by sensing the presence of air (i.e., no more replacement fluid) and the net ultrafiltration goal has been achieved; or (ii) the time prescribed for the session has elapsed.

Hemofiltration can also be performed without an ultrafiltration function (which can be called balanced hemofiltration). This mode can be used for persons that experience no weight gains between treatment sessions. This mode can also be used at the end of a hemofiltration session, when the net ultrafiltration goal was achieved before exhausting the supply of replacement fluid.

During another hemofiltration modality (called only net ultrafiltration), only a net ultrafiltration volume of waste is removed from the person. No fluid is replaced. This mode can be used when it is desired only to remove fluid. This mode can also be used at the end of a hemofiltration session, when the net ultrafiltration goal has not been achieved but the supply of replacement fluid has been exhausted.

In another hemofiltration modality (called replacement fluid bolus), there are no fluid balancing and ultrafiltration functions. Blood is circulated in an extracorporeal path and a bolus of replacement fluid is added. In the illustrated embodiment, the ultrafiltration pump 144 is run in reverse at a speed equal to the waste and replacement pump 152. This recirculates waste fluid through the waste compartments 212R and 214R, to add replacement fluid from the replacement compartments 212F and 214F to the patient. The waste fluid that is recirculated limits waste fluid removal through the hemofilter 34, yielding replacement fluid addition without additional waste fluid removal. The net volume of added replacement fluid conveyed to the patient equals the volume of waste fluid recirculated. This mode can be used to return fluid to a person in a bolus volume, e.g., during a hypotensive episode or during rinse back at the end of a given hemofiltration session.

1. Controlling the Blood Flow Rate

High blood flow rates (e.g., in some embodiments at least 200 ml/min or more, in other embodiments at least 300 ml/min or more, in other embodiments at least 400 ml/min or more, in other embodiments at least 500 ml/min or more, and in other embodiments at least 600 ml/min or more) are conducive to rapid, efficient frequent hemofiltration. The high blood flow rates not only reduce the processing time, but also significantly increases the transport rate of uremic toxins across the hemofiltration membrane. In this way, the system 10 removes high concentrations of uremic toxins, without requiring the removal of high fluid volumes, with the attendant loss of electrolytes.

The blood flow rate (BFR) can be prescribed by an attending physician and input by the operator at the beginning of a treatment session. Alternatively, the machine 16 can automatically control to achieve an optimal BFR and minimize procedure time, based upon a desired filtration fraction value (FF), ultrafiltration flow rate (UFR), and replacement fluid flow rate (RFR), as follows: BFR=(RFR+UFR)/FF where:

FF is the desired percentage of fluid to be removed from the blood stream through the hemofilter 34.

A desired FF (typically 20% to 35%) for post dilution HF can be either preset or prescribed by the attending physician. A desired FF takes into account the desired therapeutic objectives of toxin removal, as well as the performance characteristics of the hemofilter 34. A nominal FF can be determined based upon empirical and observed information drawn from a population of individuals undergoing hemofiltration. A maximum value of approximately 30% is believed to be appropriate for most individuals and hemofilters 34, to achieve a desired therapeutic result without clogging of the hemofilter 34.

In the illustrated embodiment, an arterial line sensor is incorporated into the extracorporeal circuit. The sensor 98 is an ultrasonic air leak detector, which also can provide the added capacity to sense flow rate.

In the illustrated embodiment, the machine 16 senses waste fluid pressure to control the blood flow rate to optimize the removal of fluid across the hemofilter 34. As arterial blood flows through the hemofilter 34 (controlled by the blood pump 92), a certain volume of waste fluid will cross the membrane into the waste line 118. The volume of waste fluid entering the waste line 118 depends upon the magnitude of the transmembrane pressure, or the pressure differential between the blood on the inside of filter fibers and the waste fluid on the outside of the fibers. As waste fluid is pumped away, the transmembrane pressure increases pushing waste fluid across membrane to replace removed waste. The transmembrane pressure is sensed by the sensor 132. The waste fluid pressure is adjusted by controlling the waste fluid removal rate through the fluid balancing compartments (i.e., through control of the waste and replacement pump 152) and through the UF pump 144.

The machine 16 monitors the waste fluid pressure at sensor 132. By keeping the pressure sensed by the sensor 132 slightly above zero (approximately 30 to 100 mmHg), the machine 16 achieves the maximum removal of fluid from the blood at the operative blood flow rate. Waste pressure values significantly higher than zero will limit removal of fluid from the blood and keep a higher percentage of waste fluid in the blood (i.e., result in a lower filtration fraction). However, this may be desirable for persons who tend to clot easier. The machine 16 can also include a waste pressure alarm to indicate when the sensed waste fluid pressure does not meet set criteria.

By sensing waste fluid pressure by sensor 132, the machine 16 also indirectly monitors arterial blood pressure and flow. At a constant blood pump speed, changes in arterial blood flow caused, e.g., by access clotting or increased arterial blood pressure, makes less waste fluid available in the waste line 118. At a given speed for pump 152, change in arterial blood flow will lower the sensed waste pressure at sensor 132 to a negative value, as fluid is now drawn across the membrane. The machine 16 adjusts for the change in arterial blood flow by correcting the waste fluid removal rate through the pump 152 and 144, to bring the waste pressure back to slightly above zero, or to another set value.

In this arrangement, a pressure sensor in the arterial blood line is not required. If the arterial pressure increases at a fixed blood pump speed, the blood flow must drop, which will result in a sensed related drop in the waste fluid pressure by the sensor 132. Adjusting the pump 152 and 144 to achieve a pressure slightly above zero corrects the reduced arterial blood flow. In this arrangement, since the waste fluid pressure is maintained at a slightly positive value, it is not possible to develop a reverse transmembrane pressure, which conveys waste fluid back to the person's blood. The maximum transmembrane pressure is the maximum venous pressure, since waste fluid pressure is held slightly positive.

In an alternative arrangement, arterial blood pressure can be measured by a sensor located upstream of the blood pump. The rate of the blood pump is set to maintain sensed arterial blood pressure at a predetermined control point. This controls the blood pump speed to a maximum rate. The control point can be determined, e.g., on a day-to-day basis, to take into account the blood access function of the person undergoing treatment. Use of an arterial pressure control point minimizes the treatment time, or, alternatively, if treatment time is fixed, the removal of waste fluid can maximized.

In this arrangement, safety alarms can be included should the sensed arterial pressure become more negative than the control point, along with a function to shut down the blood pump should an alarm occur.

In an alternative arrangement, a flow rate sensor can be placed in the arterial blood line to sense an actual blood flow rate. The sensed blood flow rate is compared to a commanded blood flow rate, and the blood pump is controlled to a commanded difference between the two flow rates. In this way, a maximum blood flow rate can be achieved. Alternatively, as arterial blood pressure can be expressed as a function of flow rate, arterial blood pressure can be derived from the sensed flow rate. The rate of the blood pump is set to maintain the derived arterial blood pressure at a predetermined control point. This controls the blood pump speed to a maximum rate. As stated above, use of an arterial pressure control point minimizes the treatment time, or, alternatively, if treatment time is fixed, the removal of waste fluid can be maximized by controlling waste fluid pressure, as described above.

2. Controlling the Replacement Fluid Flow Rate

RFR can be prescribed by an attending physician and inputted by the operator at the beginning of a treatment session.

Alternatively, the machine 16 can automatically control RFR to minimize procedure time based upon the desired filtration fraction value (FF), BFR, and UFR, as follows: RFR=(BFR*FF)−UFR.

In the illustrated embodiment, waste is conveyed to the waste side compartments 212R and 214R, and replacement fluid is conveyed to the replacement side compartments 212F and 214F, by operation of the dual header waste and replacement fluid pump 152. Alternatively, separate waste and replacement fluid pumps can be provided.

The speed of the waste and replacement pump 152 is controlled to achieve the desired RFR. The machine 16 cycles the inlet and outlet valve assemblies 244, 246, 248, and 250, as described. The machine 16 cycles between the valve states according to the speed of the waste and fluid pump 152 to avoid overfilling the compartments 212, 214 receiving fluid. Various synchronization techniques can be used.

In a preferred embodiment, the waste fluid is pumped at RFR, and the replacement fluid is pumped at a higher rate, but is subject to pressure relief through the pressure relief path 240 upon filling the corresponding replacement side compartment 212F and 214F.

In another arrangement, the timing of the transition between valve cycles is determined by active sensing of pressure within the compartments 212, 214 receiving liquid. As the two matching walls of chambers 212R/212F and 214R/214F reach the end of their travels, pressure will increase, signaling an end of cycle to switch valve states.

In yet another arrangement, the location of the two matching walls of chambers 212R/212F and 214R/214F as they reach the end of their travels are actively sensed by end of cycle sensors on the machine 16. The sensors can comprise, e.g., optical sensors, capacitance sensors, magnetic Hall effect sensors, or by radio frequency (e.g., microwave) sensors. The termination of movement of the walls indicates the complete filling of a compartment and the concomitant emptying of the other compartment, marking the end of a cycle. The sensors trigger an end of cycle signal to switch valve states.

The machine 16 counts the valve cycles. Since a known volume of replacement fluid is expelled from a replacement side compartment during each valve cycle, the machine 16 can derive the total replacement volume from the number of valve cycles. The replacement fluid volume is also known by the number of replacement fluid bags of known volume that are emptied during a given session.

Hemofiltration can be conducted without fluid replacement, i.e., only net ultrafiltration, by setting RFR to zero.

3. Controlling the Ultrafiltration Flow Rate

UFR can be prescribed by an attending physician and inputted by the operator at the beginning of a treatment session.

The speed of the ultrafiltration pump is monitored and varied to maintain UFR.

Frequent hemofiltration can be conducted without an ultrafiltration function, i.e., balanced hemofiltration, by setting UFR to zero.

4. Active Filtration Rate Control

In an alternative embodiment, the machine 16 also actively controls the filtration rate along with the blood flow rate, to achieve a desired magnitude of uremic toxin removal through the hemofilter 34.

In this embodiment, the machine 16 includes a flow restrictor which is positioned to engage a region of the venous blood return path 84 in the circuit 18. The restrictor comprises, e.g., a stepper-driven pressure clamp, which variably pinches a region of the venous blood return path upon command to alter the outlet flow rate of blood. This, in turn, increases or decreases the transmembrane pressure across the filter membrane.

For a given blood flow rate, waste transport across the filter membrane will increase with increasing transmembrane pressure, and vice versa. However, at some point, an increase in transmembrane pressure, aimed at maximizing waste transport across the filter membrane, will drive cellular blood components against the filter membrane. Contact with cellular blood components can also clog the filter membrane pores, which decreases waste transport through the membrane.

Filtration rate control can also rely upon an upstream sensor mounted on the machine 16. The sensor is positioned for association with a region of the arterial blood supply path between the blood pump 92 and the inlet of the hemofilter 34. The sensor senses the hematocrit of the blood prior to its passage through the filter membrane (which will be called the pre-treatment hematocrit). In the arrangement, a downstream sensor is also mounted on the machine 16. The sensor is positioned for association with a region of the venous blood return path downstream of the outlet of the hemofilter 34. The sensor senses the hematocrit of the blood after its passage through the hemofilter 34 (which will be called the post-treatment hematocrit).

The difference between pre-treatment and post-treatment hematocrit is a function of the degree of waste fluid removal by the hemofilter 34. That is, for a given blood flow rate, the more waste fluid that is removed by the hemofilter 34, the greater the difference will be between the pre-treatment and post-treatment hematocrits, and vice versa. The machine 16 can therefore derive an actual blood fluid reduction ratio based upon the difference detected by sensors between the pre-treatment and post-treatment hematocrits. The machine 16 periodically compares the derived fluid reduction value, based upon hematocrit sensing by the sensors, with the desired FF. The machine 16 issues a command to the flow restrictor to bring the difference to zero.

Waste fluid removal optimization can also be achieved by maintaining a maximum specified transmembrane pressure in the hemofilter by manipulating blood flow rate, and/or venous blood pressure, and/or waste fluid pressure. This optimization technique can be undertaken once at the outset of a given procedure, or at several intervals during the course of a procedure. In this arrangement, arterial blood pressure sensing (or derivation thereof based upon flow rate sensing) is implemented to achieve a maximum blood flow rate. A fixed or variable flow restrictor is placed in the venous blood return path to maintain a set maximum transmembrane pressure (e.g., 600 mmHg) while the maximum arterial blood flow rate is maintained. Pressure is sensed in the venous blood return path to assure that venous pressure does not exceed a set maximum amount (e.g., 250 mmHg), which is set for safety reasons. Waste fluid pressure is kept slightly above 50 mmHg. Together, control of transmembrane pressure at the maximum blood flow rate and control of waste fluid pressure at a maximum blood flow rate, maximize the waste fluid removal rate.

5. Set Up Pressure Testing/Priming

Upon mounting the disposable fluid circuit 18 on the machine 16, the pumps can be operated in forward and reverse modes and the valves operated accordingly to establish predetermined pressure conditions within the circuit. The sensors monitor build up of pressure within the circuit, as well as decrease in pressure over time. In this way, the machine can verify the function and integrity of pumps, the pressure sensors, the valves, and the flow paths overall.

The machine 16 can also verify the accuracy of the ultrafiltration pump using the fluid balancing containers.

Priming can be accomplished at the outset of each hemofiltration session to flush air and any residual fluid from the disposable fluid circuit. Fluid paths from the blood lines to the waste bag are flushed with replacement fluid. Replacement fluid is also circulated through the fluid balancing containers into the waste bag and the venous return path. The higher flow rate in the replacement fluid path and timing of the fluid balancing valve elements assure that the replacement fluid compartments completely fill and the waste fluid compartments completely empty during each cycle for priming.

6. Rinse Back

As previously described, waste fluid pressure is controlled and monitored to assure its value is always positive. Likewise, pressure between the blood pump and the hemofilter must also be positive, so that air does not enter this region of the circuit. Forward operation of the blood pump to convey arterial blood into the hemofilter establishes this positive pressure condition.

In this arrangement, no air sensing is required in the blood line, and a pressure sensor between the blood pump and the hemofilter is required.

7. Using the GUI

When configured to guide an operator to perform hemofiltration, or another treatment modality, the GUI 324 (see FIG. 19) can, e.g., include an array of icon-based touch button controls 326, 328, 330, and 332. For example, the controls can include an icon-based treatment start/select touch button 326, an icon-based treatment stop touch button 328, an icon-based audio alarm mute touch button 330, and an icon-based add fluid touch button 332.

An array of three numeric entry and display fields can appear between the icon-based touch buttons. The fields can comprise information display bars 334, 336, and 338, each with associated touch keys 340 to incrementally change the displayed information.

The associated touch keys 340 can be provided to point up (to increase the displayed value) or down (to decrease the displayed value), to intuitively indicate their function. The display bars 334, 336, and 338 and touch keys 340 can be shaded in different colors.

An array of status indicator bars can appear across the top of the screen. The left bar 342, when lighted, displays a safe color (e.g., green) to indicate a safe operation condition. The middle bar 344, when lighted, displays a cautionary color (e.g., yellow) to indicate a caution or warning condition and may, if desired, display a numeric or letter identifying the condition. The right bar 346, when lighted, displays an alarm color (e.g., red) to indicate a safety alarm condition and may, if desired, display a numeric or letter identifying the condition.

The display can also a processing status touch button 348. For example, the button 348, when touched, can change for a period of time (e.g., 5 seconds) the values displayed in the information display bars 334, 336, and 338, to show the corresponding current real time values, e.g., for a hemofiltration modality, the replacement fluid volumes exchanged (in the top display bar 334), the ultrafiltrate volume (in the middle display bar 336), and the blood volume processed (in the bottom display bar 338). The status button 348, when touched, can also show the elapsed procedure time in the left status indicator bar 342.

The display can also include a cartridge status icon 350. The icon 350, when lighted, can indicate that the cartridge 18 can be installed or removed from the machine 16.

In a preferred arrangement, the GUI 324 can employ a touch button input verification function, which monitors the information provided by the touch button controls. The input verification function inputs the information provided by a given touch button control both to the system control processor and to the system safety processor. The two processors communicate using an appropriate handshake protocol when the information received by the system control processor matches the information received by the system safety processor. The handshake allows information input to proceed for execution. The lack of a handshake between the system control processor and system safety processor indicates a possible information input error. In this instance, the GUI generates an error signal which requires a re-entry of the information input and a subsequent handshake before information input can proceed for execution.

As FIG. 19 shows, the interface can also include an infrared port 360 to support the telemetry function, as already described.

The GUI 324, though straightforward and simplified, enables the operator to set these various processing parameters for a given hemofiltration session in different ways.

For example, in one input mode for hemofiltration, the GUI 324 can prompt the operator by back-lighting the replacement fluid display bar 334, the ultrafiltration display bar 336, and the blood flow rate display bar 338. The operator follows the lights and enters the desired processing values using the associated touch up/down buttons 340. The GUI back-lights the start/select touch button 326, prompting the operator to begin the treatment. In this mode, the machine 16 controls the pumps to achieve the desired replacement fluid, ultrafiltration, and blood flow rates set by the operator. The machine terminates the procedure when all the replacement fluid is used and the net ultrafiltration goal is achieved.

In another input mode for hemofiltration, the operator can specify individual processing objectives, and the machine 16 will automatically set and maintain appropriate pump values to achieve these objectives. This mode can be activated, e.g., by pressing the start/select touch button 326 while powering on the machine 16. The GUI 324 changes the function of the display bars 334 and 336, so that the operator can select and change processing parameters. In the illustrated embodiment, the processing parameters are assigned identification numbers, which can be scrolled through and selected for display in the top bar 334 using the touch up/down keys 340. The current value for the selected parameter is displayed in the middle display bar 336, which the operator can change using the touch up/down keys 340.

In this way, the operator can, e.g., specify a desired filtration factor value (FF) along with a desired ultrafiltration flow rate (UFR) and replacement fluid flow rate (RFR). The machine will automatically control the blood pump rate (BFR), based upon the relationship BFR=(RFR+UFR)/FF, as already described.

Alternatively, the operator can specify a desired filtration factor value (FF) along with a desired ultrafiltration flow rate (UFR) and blood flow rate (BFR). The machine will automatically control the replacement fluid pump rate (RFR), based upon the relationship RFR=(BFR*FF)−UFR, as already described.

Alternatively, the operator can specify only an ultrafiltration volume. In this arrangement, the machine 16 senses waste fluid pressure to automatically control the blood flow rate to optimize the removal of fluid across the hemofilter 34, as previously described. Alternatively, the machine can automatically control the blood flow rate to optimize removal of fluid based a set control arterial blood pressure, as also already described. Still alternatively, the machine can automatically optimize the ultrafiltration flow rate and blood flow rate to achieve the desired net ultrafiltration volume.

In another mode, the operator can specify both replacement fluid volume and ultrafiltration volume to remove. In this arrangement, the machine performs a countdown of the sum of the two fluid volumes to minimize the duration of the treatment.

While particular devices and methods have been described, once this description is known, it will be apparent to those of ordinary skill in the art that other embodiments and alternative steps are also possible without departing from the spirit and scope of the invention. Moreover, it will be apparent that certain features of each embodiment can be used in combination with devices illustrated in other embodiments. Accordingly, the above description should be construed as illustrative, and not in a limiting sense, the scope of the invention being defined by the following claims.

What is claimed is:

1. A blood treatment system, comprising:
 a blood processing machine having first and second parts that are connected together, the first and second parts being movable with respect to each other and being configured to separate to define a gap between a first face of the first part and a first face of the second part in a loading configuration and to come together to close the gap in an operating configuration, the first part first face opposing the second part first face;
 a cartridge with a fluid circuit supported by the cartridge, the cartridge having a front face, a back face, a top edge, a bottom edge, and side edges, the fluid circuit and the cartridge being configured to fit into the gap;
 the blood processing machine having actuators and pumps facing the gap and configured to engage with portions of the fluid circuit when the blood processing machine is placed in the operating configuration with the cartridge in the gap; and
 a support mechanism between the first faces of the first and second parts of the blood processing machine, the support mechanism being configured such that the bottom edge of the cartridge can be rested thereon in the loading configuration so as to support the cartridge and to align the portions of the fluid circuit with said actuators and pumps for engagement of the portions of the fluid circuit therewith,
 wherein at least the side edges of the cartridge are free from contact with the support mechanism when the cartridge is rested thereon,
 wherein the bottom edge of the cartridge includes engagement surfaces that, upon the cartridge being inserted vertically into the blood processing machine, engage portions of the support mechanism such that the cartridge is progressively self-aligned with the actuators and pumps of the blood processing machine, and
 wherein the cartridge is configured such that it is progressively aligned in a lateral direction as the engagement surfaces travel along portions of the support mechanism toward a vertical travel limit.

2. A system as in claim 1, wherein the support mechanism is configured such that the cartridge can be positioned in the gap in a single vertical motion.

3. A system as in claim 1, wherein the blood processing machine has a base on the first part such that the first part is fixed and the second part moves relative to the base.

4. A system as in claim 1, further comprising a latch, wherein the first part is secured to the second part by said latch when the blood processing machine is placed in the operating configuration.

5. A system as in claim 1, wherein an operator interface is positioned on a second face of the second part such that the operator interface fits substantially within a front view of the blood processing machine.

6. A system as in claim 1, wherein the blood processing machine has a front view with a frontal area with a top edge and side edges;
 the first part has a chassis panel with pump rotors, line clamps, and sensors extending over substantially the entire first face thereof, the chassis panel facing the gap and extending fully between the blood processing machine side edges and from the support mechanism to the blood processing machine top edge.

7. A system as in claim 1, wherein a movement of the first and second parts from a loading configuration to an operating configuration engages the portions of the fluid circuit with the actuators and pumps and further supports the cartridge.

8. A system as in claim 1, wherein the first and second parts are displaceable relative to each other such that an angular orientation of the second part with respect to the first part is kept the same as the blood processing machine changes between the loading and operating configurations.

9. A system as in claim 8, wherein the first face of the first part remains parallel to the first face of the second part as the blood processing machine changes between the loading and operating configurations.

10. A system as in claim 1, wherein the fluid circuit is engageable with the actuators and the pumps and includes blood lines connectable to a patient blood access and fluids lines connectable to a source of fluid used in performing a blood treatment.

11. A system as in claim 1, wherein the support mechanism is configured to maintain alignment of the portions of the fluid circuit with the actuators and pumps when the blood processing machine changes from the loading configuration to the operating configuration.

12. A system as in claim 1, wherein the support mechanism is arranged such that the front face of the cartridge is parallel to the first face of the first part when the cartridge is rested on the support mechanism in the loading configuration and such that the front face of the cartridge remains parallel to the first face of the first part in the operating configuration.

13. A system as in claim 1, wherein the first part includes a peristaltic pump actuator and the second part includes a pump race, the peristaltic pump actuator and the pump race contacting the portions of the fluid circuit when the blood processing machine is in the operating configuration.

14. A system as in claim 1, wherein the second part includes a pump race that is biased with respect to the second part such that the pump race is urged against the portions of the fluid circuit when the blood processing machine is in the operating configuration.

15. A system as in claim 1, wherein the cartridge is laterally aligned with actuators and pumps on at least the first face of the first part as a result of, and immediately upon, being rested on the support mechanism in the loading configuration.

16. A system as in claim 1, wherein the cartridge is laterally aligned with actuators and pumps on both the first and second parts as a result of, and immediately upon, being rested on the support mechanism in the loading configuration.

17. A system as in claim 1, wherein the cartridge has at least one indentation adapted to interact with the support mechanism such that the cartridge fits on the support mechanism in an orientation with the actuators and pumps aligned to said portions of the fluid circuit and such that a movement of the first and second parts together to the operating configuration engages the actuators and pumps with said portions of the fluid circuit.

18. A system as in claim 1, wherein the cartridge only contacts the blood processing machine at the cartridge bottom edge when the cartridge is rested on the support mechanism in the loading configuration.

19. A system as in claim 1, wherein said cartridge bottom edge includes at least one recess configured to engage with the support mechanism when the cartridge is rested thereon.

20. A system as in claim 19, wherein said support mechanism includes at least one rail, the at least one recess configured to engage with a respective surface of the at least one rail.

21. A system as in claim 20, wherein the at least one recess is shaped complementary to a respective contact surface of the at least one rail.

* * * * *